(12) United States Patent  
Liberty et al.

(10) Patent No.: US 7,236,156 B2
(45) Date of Patent: Jun. 26, 2007

(54) METHODS AND DEVICES FOR IDENTIFYING USERS BASED ON TREMOR

(75) Inventors: Matthew G. Liberty, Potomac, MD (US); Christopher D. Roller, Fairfax, VA (US); Daniel S. Simpkins, Bethesda, MD (US); Charles W. K. Gritton, Sterling, VA (US)

(73) Assignee: Hillcrest Laboratories, Inc., Rockville, MD (US)

( * ) Notice: Subject to any disclaimer, the term of this patent is extended or adjusted under 35 U.S.C. 154(b) by 0 days.

(21) Appl. No.: 11/119,688

(22) Filed: May 2, 2005

(65) Prior Publication Data

US 2005/0243061 A1    Nov. 3, 2005

Related U.S. Application Data

(60) Provisional application No. 60/612,571, filed on Sep. 23, 2004, provisional application No. 60/566,444, filed on Apr. 30, 2004.

(51) Int. Cl.
  G09G 5/08    (2006.01)
  G09G 5/00    (2006.01)

(52) U.S. Cl. ............... 345/158; 345/156; 345/157; 345/163

(58) Field of Classification Search ........ 345/173–179, 345/156–169; 178/18.01–18.07, 19.01–19.06
See application file for complete search history.

(56) References Cited

U.S. PATENT DOCUMENTS

| | | | |
|---|---|---|---|
| 4,787,051 A | 11/1988 | Olson | |
| 4,839,838 A | 6/1989 | LaBiche et al. | |
| 5,045,843 A | 9/1991 | Hansen | |
| 5,138,154 A | 8/1992 | Hotelling | |
| 5,181,181 A * | 1/1993 | Glynn | 702/141 |
| 5,359,348 A | 10/1994 | Pilcher et al. | |
| 5,440,326 A | 8/1995 | Quinn | |
| 5,698,784 A | 12/1997 | Hotelling et al. | |
| 5,703,623 A | 12/1997 | Hall et al. | |
| 5,825,350 A | 10/1998 | Case, Jr. et al. | |
| 5,835,156 A | 11/1998 | Blonstein et al. | |
| 5,898,421 A | 4/1999 | Quinn | |
| 5,912,612 A | 6/1999 | DeVolpi | |
| 5,955,988 A | 9/1999 | Blonstein et al. | |
| 6,002,394 A | 12/1999 | Schein et al. | |
| 6,016,144 A | 1/2000 | Blonstein et al. | |
| 6,049,823 A | 4/2000 | Hwang | |
| 6,492,981 B1 | 12/2002 | Stork et al. | |
| 6,753,849 B1 | 6/2004 | Curran et al. | |

(Continued)

OTHER PUBLICATIONS

Navarrete, P., et al., "Eigensapce-based Recognition of Faces: Comparisons and a new Approach," Image Analysis and Processing, 2001, pp. 1-6.

(Continued)

*Primary Examiner*—Vijay Shankar
(74) *Attorney, Agent, or Firm*—Potomac Patent Group PLLC

(57) ABSTRACT

Systems and methods according to the present invention address these needs and others by providing a handheld device, e.g., a 3D pointing device, which uses hand tremor as an input. One or more sensors within the handheld device detect a user's hand tremor and identify the user based on the detected tremor.

77 Claims, 11 Drawing Sheets

U.S. PATENT DOCUMENTS

| | | |
|---|---|---|
| 6,933,923 B2 | 8/2005 | Feinstein |
| 6,990,639 B2 | 1/2006 | Wilson |
| 6,998,966 B2 | 2/2006 | Pedersen et al. |
| 2003/0107551 A1 | 6/2003 | Dunker |
| 2004/0095317 A1 | 5/2004 | Zhang et al. |
| 2004/0239626 A1 | 12/2004 | Noguera |
| 2004/0268393 A1 | 12/2004 | Hunleth et al. |
| 2005/0174324 A1 | 8/2005 | Liberty et al. |
| 2005/0212767 A1 | 9/2005 | Marvit et al. |
| 2005/0243062 A1 | 11/2005 | Liberty |
| 2005/0253806 A1 | 11/2005 | Liberty et al. |
| 2006/0028446 A1 | 2/2006 | Liberty et al. |

OTHER PUBLICATIONS

Jakubowski, J., et al., "Higher Order Statistics and Neural Network for Tremor Recognition," IEEE Transactions on Biomedical Engineering, vol. 49, No. 2, Feb. 2002, pp. 152-159.

Liu, C., et al., "Enhanced Fisher Linear Discriminant Models for Face Recognition," 14th International Conference on Pattern Recognition, Queensland, Australia, Aug. 17-20, 1998, pp. 1-5.

International Search Report for PCT/US05/15096, mailed May 15, 2006.

Written Opinion for PCT/US05/15096, mailed May 15, 2006.

International Search Report for PCT/US04/35369, mailed May 11, 2006.

Written Opinion for PCT/US04/35369, mailed May 11, 2006.

Geen, J., et al., "New iMEMS Angular-Rate-Sensing Gyroscope," Analog Dialogue, 37-03 (2003), pp. 1-4.

* cited by examiner

METHODS AND DEVICES FOR IDENTIFYING USERS BASED ON TREMOR

RELATED APPLICATIONS

This application is related to, and claims priority from, U.S. Provisional Patent Application Ser. No. 60/566,444 filed on Apr. 30, 2004, entitled "Freespace Pointing Device", the disclosure of which is incorporated here by reference. This application is also related to, and claims priority from, U.S. Provisional Patent Application Ser. No. 60/612,571, filed on Sep. 23, 2004, entitled "Free Space Pointing Devices and Methods", the disclosure of which is incorporated here by reference. This application is also related to U.S. patent applications Ser. Nos. 11/119,987, 11/119,719, and 11/119,663, entitled "Methods and Devices for Removing Unintentional Movement in 3D Pointing Devices", "3D Pointing Devices with Tilt Compensation and Improved Usability", "3D Pointing Devices and Methods", all of which were filed concurrently here with and all of which are incorporated here by reference.

BACKGROUND

The present invention describes techniques and devices for identifying the user of a device, e.g., a handheld device, based on tremor associated with the user's holding of the device. According to some exemplary embodiments of the present invention, the handheld device can be a three-dimensional (hereinafter "3D") pointing device.

Technologies associated with the communication of information have evolved rapidly over the last several decades. Television, cellular telephony, the Internet and optical communication techniques (to name just a few things) combine to inundate consumers with available information and entertainment options. Taking television as an example, the last three decades have seen the introduction of cable television service, satellite television service, pay-per-view movies and video-on-demand. Whereas television viewers of the 1960s could typically receive perhaps four or five over-the-air TV channels on their television sets, today's TV watchers have the opportunity to select from hundreds, thousands, and potentially millions of channels of shows and information. Video-on-demand technology, currently used primarily in hotels and the like, provides the potential for in-home entertainment selection from among thousands of movie titles.

The technological ability to provide so much information and content to end users provides both opportunities and challenges to system designers and service providers. One challenge is that while end users typically prefer having more choices rather than fewer, this preference is counterweighted by their desire that the selection process be both fast and simple. Unfortunately, the development of the systems and interfaces by which end users access media items has resulted in selection processes which are neither fast nor simple. Consider again the example of television programs. When television was in its infancy, determining which program to watch was a relatively simple process primarily due to the small number of choices. One would consult a printed guide which was formatted, for example, as series of columns and rows which showed the correspondence between (1) nearby television channels, (2) programs being transmitted on those channels and (3) date and time. The television was tuned to the desired channel by adjusting a tuner knob and the viewer watched the selected program. Later, remote control devices were introduced that permitted viewers to tune the television from a distance. This addition to the user-television interface created the phenomenon known as "channel surfing" whereby a viewer could rapidly view short segments being broadcast on a number of channels to quickly learn what programs were available at any given time.

Despite the fact that the number of channels and amount of viewable content has dramatically increased, the generally available user interface, control device options and frameworks for televisions has not changed much over the last 30 years. Printed guides are still the most prevalent mechanism for conveying programming information. The multiple button remote control with up and down arrows is still the most prevalent channel/content selection mechanism. The reaction of those who design and implement the TV user interface to the increase in available media content has been a straightforward extension of the existing selection procedures and interface objects. Thus, the number of rows in the printed guides has been increased to accommodate more channels. The number of buttons on the remote control devices has been increased to support additional functionality and content handling, e.g., as shown in FIG. 1. However, this approach has significantly increased both the time required for a viewer to review the available information and the complexity of actions required to implement a selection. Arguably, the cumbersome nature of the existing interface has hampered commercial implementation of some services, e.g., video-on-demand, since consumers are resistant to new services that will add complexity to an interface that they view as already too slow and complex.

In addition to increases in bandwidth and content, the user interface bottleneck problem is being exacerbated by the aggregation of technologies. Consumers are reacting positively to having the option of buying integrated systems rather than a number of segregable components. An example of this trend is the combination television/VCR/DVD in which three previously independent components are frequently sold today as an integrated unit. This trend is likely to continue, potentially with an end result that most if not all of the communication devices currently found in the household will be packaged together as an integrated unit, e.g., a television/VCR/DVD/internet access/radio/stereo unit. Even those who continue to buy separate components will likely desire seamless control of, and interworking between, the separate components. With this increased aggregation comes the potential for more complexity in the user interface. For example, when so-called "universal" remote units were introduced, e.g., to combine the functionality of TV remote units and VCR remote units, the number of buttons on these universal remote units was typically more than the number of buttons on either the TV remote unit or VCR remote unit individually. This added number of buttons and functionality makes it very difficult to control anything but the simplest aspects of a TV or VCR without hunting for exactly the right button on the remote. Many times, these universal remotes do not provide enough buttons to access many levels of control or features unique to certain TVs. In these cases, the original device remote unit is still needed, and the original hassle of handling multiple remotes remains due to user interface issues arising from the complexity of aggregation. Some remote units have addressed this problem by adding "soft" buttons that can be programmed with the expert commands. These soft buttons sometimes have accompanying LCD displays to indicate their action. These too have the flaw that they are difficult to use without looking away from the TV to the remote control. Yet another flaw in these remote units is the use of modes in an attempt to reduce the number of buttons. In these "moded" universal remote units, a special button exists to select whether the remote should communicate with the TV, DVD player, cable set-top box, VCR, etc. This causes many usability issues including sending commands to the wrong device, forcing the user to look at the remote to make sure that it is in the right mode, and it does not provide any simplification to the integration of multiple devices. The most advanced of these universal remote units provide some integration by allowing the user to program sequences of commands to multiple devices into the remote. This is such a difficult task that many users hire professional installers to program their universal remote units.

Some attempts have also been made to modernize the screen interface between end users and media systems. However, these attempts typically suffer from, among other drawbacks, an inability to easily scale between large collections of media items and small collections of media items. For example, interfaces which rely on lists of items may work well for small collections of media items, but are tedious to browse for large collections of media items. Interfaces which rely on hierarchical navigation (e.g., tree structures) may be speedier to traverse than list interfaces for large collections of media items, but are not readily adaptable to small collections of media items. Additionally, users tend to lose interest in selection processes wherein the user has to move through three or more layers in a tree structure. For all of these cases, current remote units make this selection processor even more tedious by forcing the user to repeatedly depress the up and down buttons to navigate the list or hierarchies. When selection skipping controls are available such as page up and page down, the user usually has to look at the remote to find these special buttons or be trained to know that they even exist. Accordingly, organizing frameworks, techniques and systems which simplify the control and screen interface between users and media systems as well as accelerate the selection process, while at the same time permitting service providers to take advantage of the increases in available bandwidth to end user equipment by facilitating the supply of a large number of media items and new services to the user have been proposed in U.S. patent application Ser. No. 10/768,432, filed on Jan. 30, 2004, entitled "A Control Framework with a Zoomable Graphical User Interface for Organizing, Selecting and Launching Media Items", the disclosure of which is incorporated here by reference.

Of particular interest for this specification are the remote devices usable to interact with such frameworks, as well as other applications and systems. As mentioned in the above-incorporated application, various different types of remote devices can be used with such frameworks including, for example, trackballs, "mouse"-type pointing devices, light pens, etc. However, another category of remote devices which can be used with such frameworks (and other applications) is 3D pointing devices. The phrase "3D pointing" is used in this specification to refer to the ability of an input device to move in three (or more) dimensions in the air in front of, e.g., a display screen, and the corresponding ability of the user interface to translate those motions directly into user interface commands, e.g., movement of a cursor on the display screen. The transfer of data between the 3D pointing device may be performed wirelessly or via a wire connecting the 3D pointing device to another device. Thus "3D pointing" differs from, e.g., conventional computer mouse pointing techniques which use a surface, e.g., a desk surface or mousepad, as a proxy surface from which relative movement of the mouse is translated into cursor movement on the computer display screen. An example of a 3D pointing device can be found in U.S. Pat. No. 5,440,326.

The '326 patent describes, among other things, a vertical gyroscope adapted for use as a pointing device for controlling the position of a cursor on the display of a computer. A motor at the core of the gyroscope is suspended by two pairs of orthogonal gimbals from a hand-held controller device and nominally oriented with its spin axis vertical by a pendulous device. Electro-optical shaft angle encoders sense the orientation of a hand-held controller device as it is manipulated by a user and the resulting electrical output is converted into a format usable by a computer to control the movement of a cursor on the screen of the computer display.

When a user holds a 3D pointing device, or any free standing device (such as a cell phone, PDA, etc.), involuntary hand movement (tremor) results in corresponding movement of the handheld device. According to the present invention, such movement is detected by one or more sensors within the handheld device and used as input to various functions, e.g., identification of the person holding the device.

SUMMARY

Systems and methods according to the present invention address these needs and others by providing a handheld device, e.g., a 3D pointing device, which uses hand tremor as an input. One or more sensors within the handheld device detect a user's hand tremor and identify the user based on the detected tremor.

According to an exemplary embodiment of the present invention, a handheld, pointing device includes a first rotational sensor for determining rotation of the pointing device about a first axis and generating a first rotational output associated therewith, a second rotational sensor for determining rotation of the pointing device about a second axis and generating a second rotational output associated therewith, an accelerometer for determining an acceleration of the pointing device and outputting an acceleration output associated therewith and a processing unit for receiving the first and second rotational outputs and the acceleration output and for: (a) establishing, during a training period, a plurality of hand tremor classes each of which is associated with a user by processing training data derived from at least one of the first and second rotational outputs and the acceleration output while the user is holding the pointing device without intentional movement; and (b) determining, subsequent to the training period, an identity of a current user of the pointing device by comparing data derived from at least one of a current first rotational output, a current second rotational output and a current acceleration output to the plurality of hand tremor classes established during the training period.

According to another exemplary embodiment of the present invention, a method for identifying a user of a handheld device includes the steps of detecting a hand tremor associated with a user holding said handheld device and identifying the user based on the detected hand tremor.

According to yet another exemplary embodiment of the present invention, a handheld device includes at least one motion sensor capable of generating data associated with movement of the handheld device and a processing unit for detecting hand tremor data based on the movement data and for identifying a user based on the hand tremor data.

BRIEF DESCRIPTION OF THE DRAWINGS

The accompanying drawings illustrate exemplary embodiments of the present invention, wherein.

DETAILED DESCRIPTION

Figure 1:
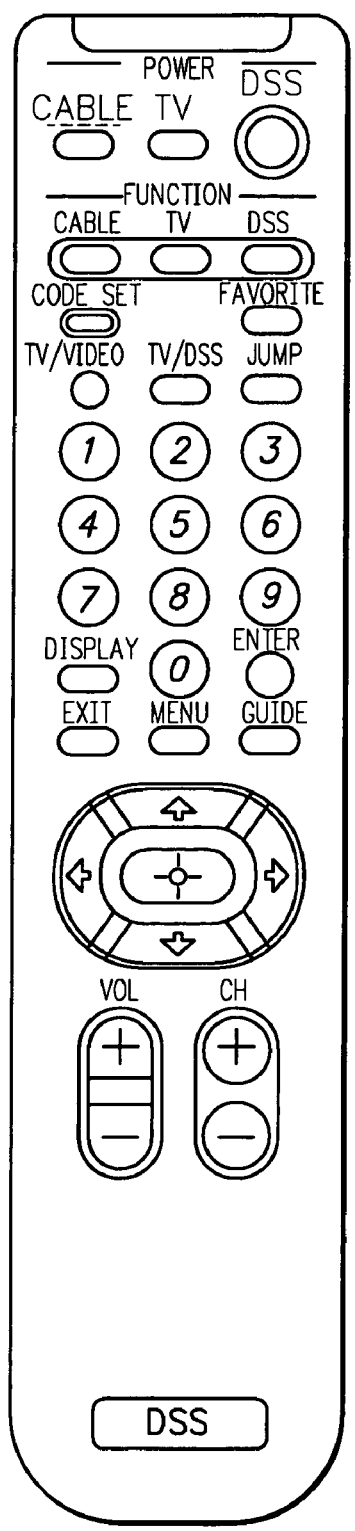
FIG. 1 depicts a conventional remote control unit for an entertainment system.

The following detailed description of the invention refers to the accompanying drawings. The same reference numbers in different drawings identify the same or similar elements. Also, the following detailed description does not limit the invention. Instead, the scope of the invention is defined by the appended claims.

In order to provide some context for this discussion, an exemplary aggregated media system 200 in which the present invention can be implemented will first be described with respect to FIG. 2. Those skilled in the art will appreciate, however, that the present invention is not restricted to implementation in this type of media system and that more or fewer components can be included therein. Therein, an input/output (I/O) bus 210 connects the system components in the media system 200 together. The I/O bus 210 represents any of a number of different of mechanisms and techniques for routing signals between the media system components. For example, the I/O bus 210 may include an appropriate number of independent audio "patch" cables that route audio signals, coaxial cables that route video signals, two-wire serial lines or infrared or radio frequency transceivers that route control signals, optical fiber or any other routing mechanisms that route other types of signals.

In this exemplary embodiment, the media system 200 includes a television/monitor 212, a video cassette recorder (VCR) 214, digital video disk (DVD) recorder/playback device 216, audio/video tuner 218 and compact disk player 220 coupled to the I/O bus 210. The VCR 214, DVD 216 and compact disk player 220 may be single disk or single cassette devices, or alternatively may be multiple disk or multiple cassette devices. They may be independent units or integrated together. In addition, the media system 200 includes a microphone/speaker system 222, video camera 224 and a wireless I/O control device 226. According to exemplary embodiments of the present invention, the wireless I/O control device 226 is a 3D pointing device according to one of the exemplary embodiments described below. The wireless I/O control device 226 can communicate with the entertainment system 200 using, e.g., an IR or RF transmitter or transceiver. Alternatively, the I/O control device can be connected to the entertainment system 200 via a wire.

The entertainment system 200 also includes a system controller 228. According to one exemplary embodiment of the present invention, the system controller 228 operates to store and display entertainment system data available from a plurality of entertainment system data sources and to control a wide variety of features associated with each of the system components. As shown in FIG. 2, system controller 228 is coupled, either directly or indirectly, to each of the system components, as necessary, through I/O bus 210. In one exemplary embodiment, in addition to or in place of I/O bus 210, system controller 228 is configured with a wireless communication transmitter (or transceiver), which is capable of communicating with the system components via IR signals or RF signals. Regardless of the control medium, the system controller 228 is configured to control the media components of the media system 200 via a graphical user interface described below.

Figure 2:
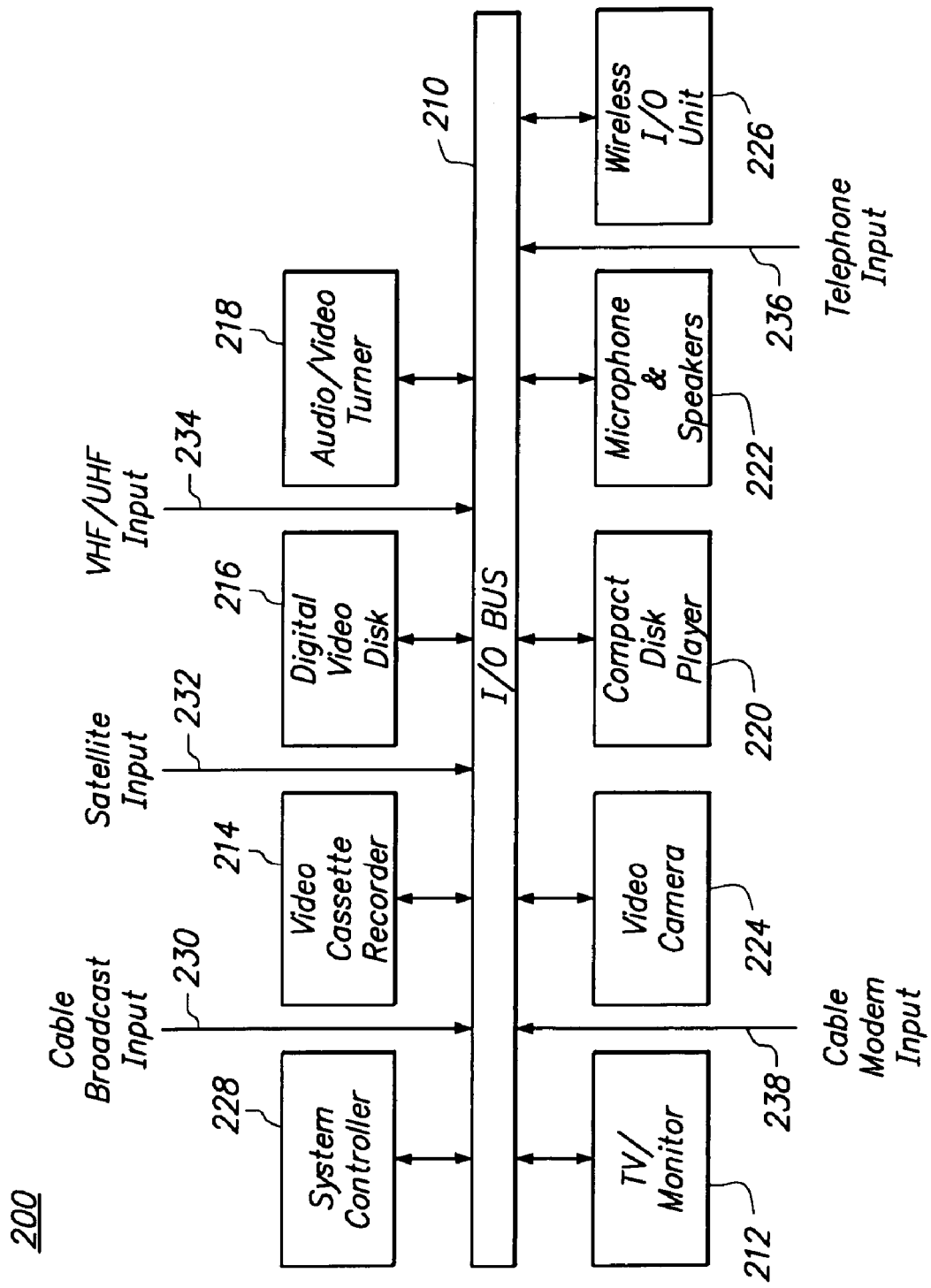
FIG. 2 depicts an exemplary media system in which exemplary embodiments of the present invention can be implemented.

As further illustrated in FIG. 2, media system 200 may be configured to receive media items from various media sources and service providers. In this exemplary embodiment, media system 200 receives media input from and, optionally, sends information to, any or all of the following sources: cable broadcast 230, satellite broadcast 232 (e.g., via a satellite dish), very high frequency (VHF) or ultra high frequency (UHF) radio frequency communication of the broadcast television networks 234 (e.g., via an aerial antenna), telephone network 236 and cable modem 238 (or another source of Internet content). Those skilled in the art will appreciate that the media components and media sources illustrated and described with respect to FIG. 2 are purely exemplary and that media system 200 may include more or fewer of both. For example, other types of inputs to the system include AM/FM radio and satellite radio.

More details regarding this exemplary entertainment system and frameworks associated therewith can be found in the above-incorporated by reference U.S. patent application "A Control Framework with a Zoomable Graphical User Interface for Organizing, Selecting and Launching Media Items". Alternatively, remote devices in accordance with the present invention can be used in conjunction with other systems, for example computer systems including, e.g., a display, a processor and a memory system or with various other systems and applications.

Figure 3:
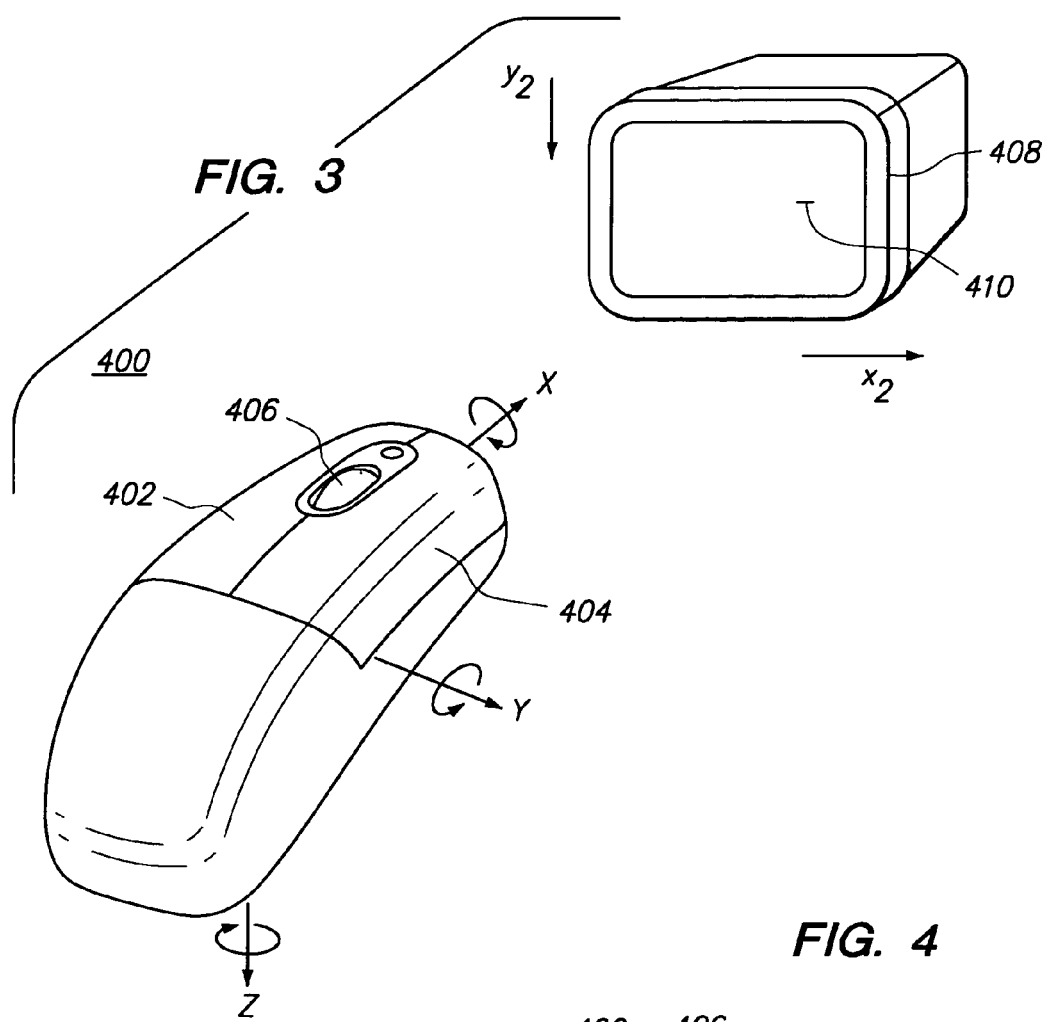
FIG. 3 shows a 3D pointing device according to an exemplary embodiment of the present invention.

As mentioned in the Background section, remote devices which operate as 3D pointers are of particular interest for the present specification. Such devices enable the translation of movement, e.g., gestures, into commands to a user interface. An exemplary 3D pointing device 400 is depicted in FIG. 3. Therein, user movement of the 3D pointing can be defined, for example, in terms of a combination of x-axis attitude (roll), y-axis elevation (pitch) and/or z-axis heading (yaw) motion of the 3D pointing device 400. In addition, some exemplary embodiments of the present invention can also measure linear movement of the 3D pointing device 400 along the x, y, and z axes to generate cursor movement or other user interface commands. In the exemplary embodiment of FIG. 3, the 3D pointing device 400 includes two buttons 402 and 404 as well as a scroll wheel 406, although other exemplary embodiments will include other physical configurations. According to exemplary embodiments of the present invention, it is anticipated that 3D pointing devices 400 will be held by a user in front of a display 408 and that motion of the 3D pointing device 400 will be translated by the 3D pointing device into output which is usable to interact with the information displayed on display 408, e.g., to move the cursor 410 on the display 408. For example, rotation of the 3D pointing device 400 about the y-axis can be sensed by the 3D pointing device 400 and translated into an output usable by the system to move cursor 410 along the $y_2$ axis of the display 408. Likewise, rotation of the 3D pointing device 408 about the z-axis can be sensed by the 3D pointing device 400 and translated into an output usable by the system to move cursor 410 along the $x_2$ axis of the display 408. It will be appreciated that the output of 3D pointing device 400 can be used to interact with the display 408 in a number of ways other than (or in addition to) cursor movement, for example it can control cursor fading, volume or media transport (play, pause, fast-forward and rewind). Input commands may include operations in addition to cursor movement, for example, a zoom in or zoom out on a particular region of a display. A cursor may or may not be visible. Similarly, rotation of the 3D pointing device 400 sensed about the x-axis of 3D pointing device 400 can be used in addition to, or as an alternative to, y-axis and/or z-axis rotation to provide input to a user interface.

Figure 4:
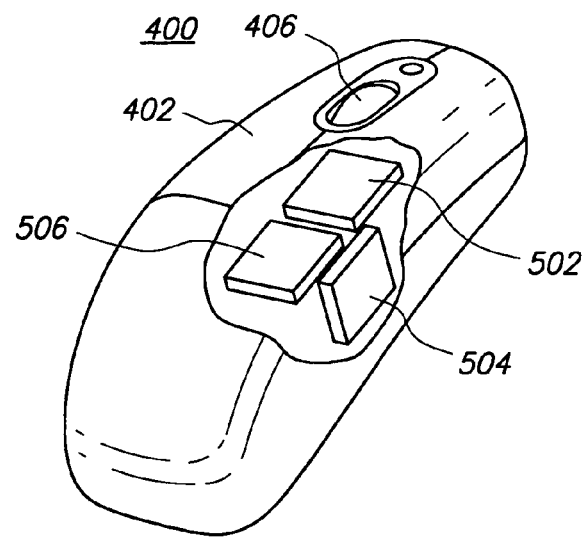
FIG. 4 illustrates a cutaway view of the 3D pointing device in FIG. 4 including two rotational sensors and one accelerometer.

According to one exemplary embodiment of the present invention, two rotational sensors 502 and 504 and one accelerometer 506 can be employed as sensors in 3D pointing device 400 as shown in FIG. 4. The rotational sensors 502 and 504 can, for example, be implemented using ADXRS150 or ADXRS401 sensors made by Analog Devices. It will be appreciated by those skilled in the art that other types of rotational sensors can be employed as rotational sensors 502 and 504 and that the ADXRS150 and ADXRS401 are purely used as an illustrative example. Unlike traditional gyroscopes, these rotational sensors use MEMS technology to provide a resonating mass which is attached to a frame so that it can resonate only along one direction. The resonating mass is displaced when the body to which the sensor is affixed is rotated around the sensor's sensing axis. This displacement can be measured using the Coriolis acceleration effect to determine an angular velocity associated with rotation along the sensing axis. If the rotational sensors 502 and 504 have a single sensing axis (as for example the ADXRS150s), then they can be mounted in the 3D pointing device 400 such that their sensing axes are aligned with the rotations to be measured. For this exemplary embodiment of the present invention, this means that rotational sensor 504 is mounted such that its sensing axis is parallel to the y-axis and that rotational sensor 502 is mounted such that its sensing axis is parallel to the z-axis as shown in FIG. 4. Note, however, that aligning the sensing axes of the rotational sensors 502 and 504 parallel to the desired measurement axes is not required since exemplary embodiments of the present invention also provide techniques for compensating for offset between axes.

One challenge faced in implementing exemplary 3D pointing devices 400 in accordance with the present invention is to employ components, e.g., rotational sensors 502 and 504, which are not too costly, while at the same time providing a high degree of correlation between movement of the 3D pointing device 400, a user's expectation regarding how the user interface will react to that particular movement of the 3D pointing device and actual user interface performance in response to that movement. For example, if the 3D pointing device 400 is not moving, the user will likely expect that the cursor ought not to be drifting across the screen. Likewise, if the user rotates the 3D pointing device 400 purely around the y-axis, she or he would likely not expect to see the resulting cursor movement on display 408 contain any significant $x_2$ axis component. To achieve these, and other, aspects of exemplary embodiments of the present invention, various measurements and calculations are performed by the handheld device 400 which are used to adjust the outputs of one or more of the sensors 502, 504 and 506 and/or as part of the input used by a processor to determine an appropriate output for the user interface based on the outputs of the sensors 502, 504 and 506. These measurements and calculations are used to compensate for factors which fall broadly into two categories: (1) factors which are intrinsic to the 3D pointing device 400, e.g., errors associated with the particular sensors 502, 504 and 506 used in the device 400 or the way in which the sensors are mounted in the device 400 and (2) factors which are not intrinsic to the 3D pointing device 400, but are instead associated with the manner in which a user is using the 3D pointing device 400, e.g., linear acceleration, tilt and tremor. Exemplary techniques for handling each of these effects are described below.

Figure 5:
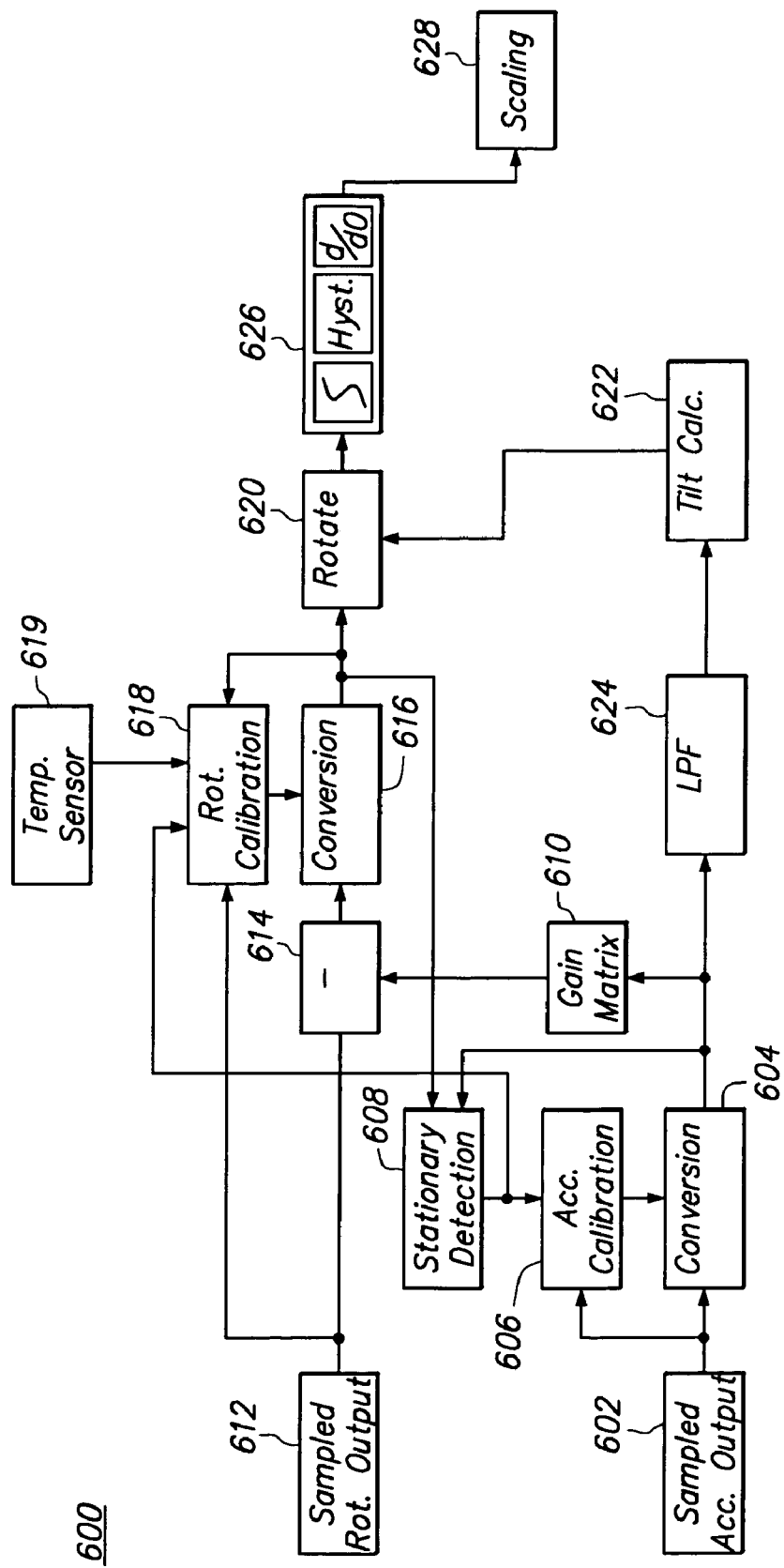
FIG. 5 is a block diagram illustrating processing of data associated with 3D pointing devices according to an exemplary embodiment of the present invention.
Figure 6A:
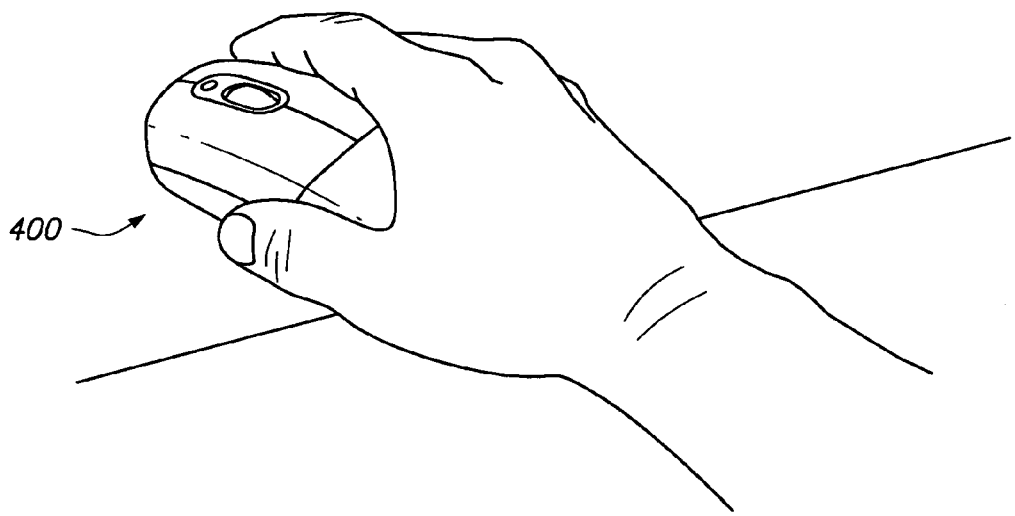
FIGS. 6(a)-6(d) illustrate the effects of tilt.
Figure 6B:
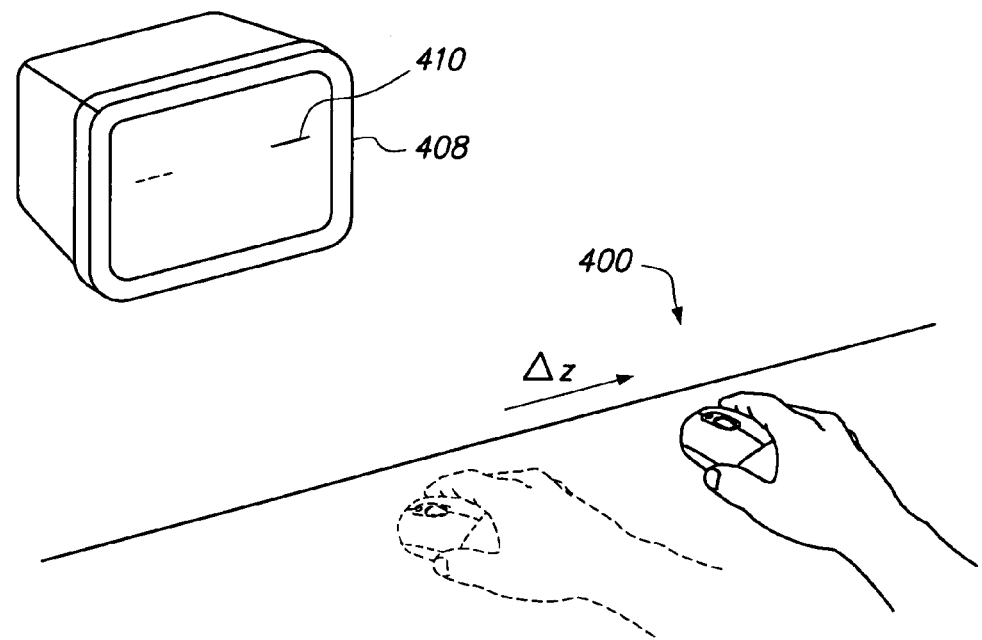
Figure 6C:
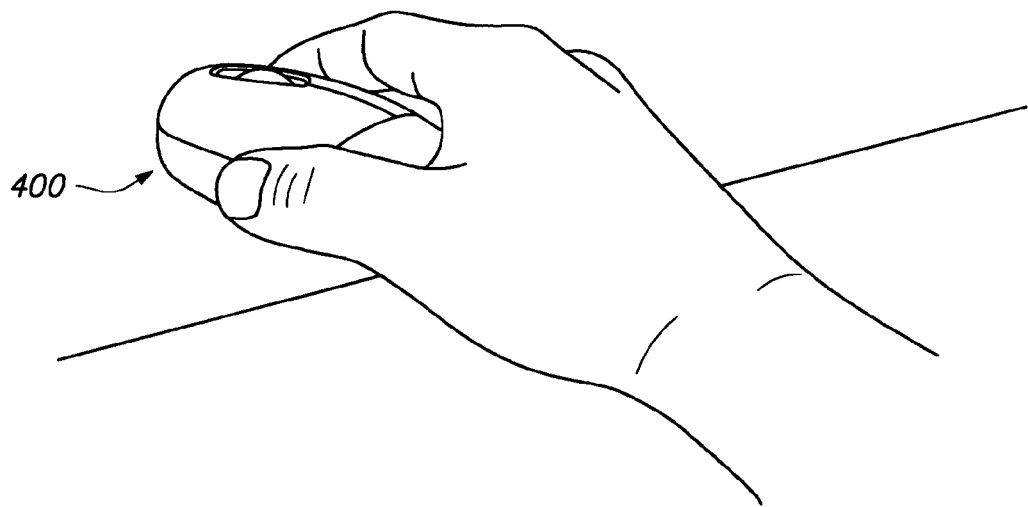
Figure 6D:
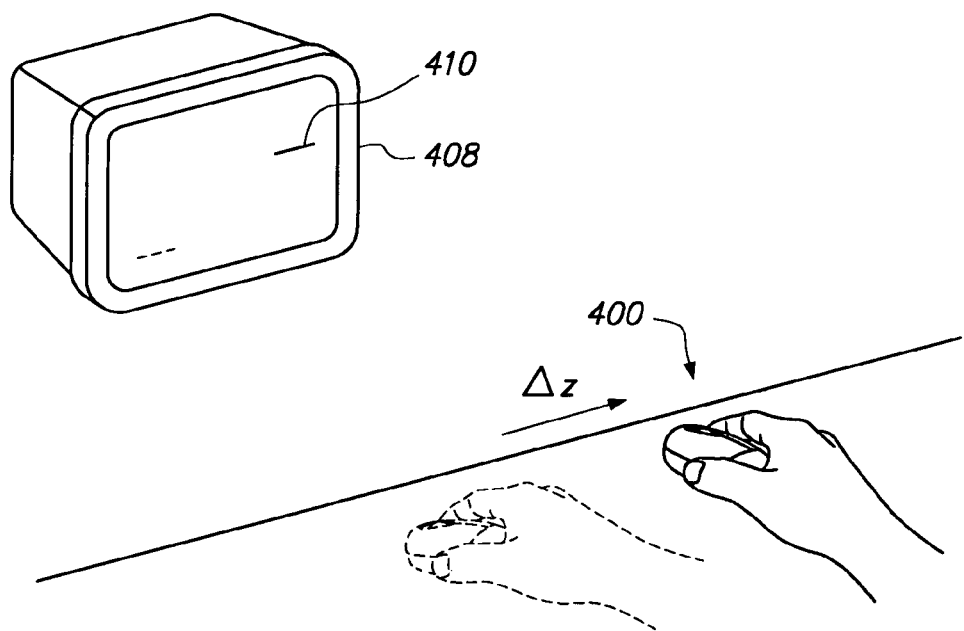

A process model 600 which describes the general operation of 3D pointing devices according to exemplary embodiments of the present invention is illustrated in FIG. 5. The rotational sensors 502 and 504, as well as the accelerometer 506, produce analog signals which are sampled periodically, e.g., 200 samples/second. For the purposes of this discussion, a set of these inputs shall be referred to using the notation (x, y, z, αy, αz), wherein x, y, z are the sampled output values of the exemplary three-axis accelerometer 506 which are associated with acceleration of the 3D pointing device in the x-axis, y-axis and z-axis directions, respectively, αy is a the sampled output value from rotational sensor 502 associated with the rotation of the 3D pointing device about the y-axis and αz is the sampled output value from rotational sensor 504 associated with rotation of the 3D pointing device 400 about the z-axis.

The output from the accelerometer 506 is provided and, if the accelerometer 506 provides analog output, then the output is sampled and digitized by an A/D converter (not shown) to generate sampled accelerometer output 602. The sampled output values are converted from raw units to units of acceleration, e.g., gravities (g), as indicated by conversion function 604. The acceleration calibration block 606 provides the values used for the conversion function 604. This calibration of the accelerometer output 602 can include, for example, compensation for one or more of scale, offset and axis misalignment error associated with the accelerometer 506. Exemplary conversions for the accelerometer data can be performed using the following equation:

$$A = S * ((M-P) \cdot * G(T)) \qquad (1)$$

wherein M is a 3×1 column vector composed of the sampled output values (x, y, z), P is a 3×1 column vector of sensor offsets, and S is a 3×3 matrix that contains both scale, axis misalignment, and sensor rotation compensation. G(T) is a gain factor that is a function of temperature. The "*" operator represents matrix multiplication and the ".*" operator represents element multiplication. The exemplary accelerometer 506 has an exemplary full range of +/−2 g. Sensor offset, P, refers to the sensor output, M, for an accelerometer measurement of 0 g. Scale refers to the conversion factor between the sampled unit value and g. The actual scale of any given accelerometer sensor may deviate from these nominal scale values due to, e.g., manufacturing variances. Accordingly the scale factor in the equations above will be proportional to this deviation.

Accelerometer 506 scale and offset deviations can be measured by, for example, applying 1 g of force along one an axis and measuring the result, R1. Then a −1 g force is applied resulting in measurement R2. The individual axis scale, s, and the individual axis offset, p, can be computed as follows:

$$s=(R1-R2)/2 \qquad (2)$$

$$p=(R1+R2)/2 \qquad (3)$$

In this simple case, P is the column vector of the p for each axis, and S is the diagonal matrix of the 1/s for each axis.

However, in addition to scale and offset, readings generated by accelerometer 506 may also suffer from cross-axes effects. Cross-axes effects include non-aligned axes, e.g., wherein one or more of the sensing axes of the accelerometer 506 as it is mounted in the 3D pointing device 400 are not aligned with the corresponding axis in the inertial frame of reference, or mechanical errors associated with the machining of the accelerometer 506 itself, e.g., wherein even though the axes are properly aligned, a purely y-axis acceleration force may result in a sensor reading along the z-axis of the accelerometer 506. Both of these effects can also be measured and added to the calibration performed by function 606.

The accelerometer 506 serves several purposes in exemplary 3D pointing devices according to exemplary embodiments of the present invention. For example, if rotational sensors 502 and 504 are implemented using the exemplary Coriolis effect rotational sensors described above, then the output of the rotational sensors 502 and 504 will vary based on the linear acceleration experienced by each rotational sensor. Thus, one exemplary use of the accelerometer 506 is to compensate for fluctuations in the readings generated by the rotational sensors 502 and 504 which are caused by variances in linear acceleration. This can be accomplished by multiplying the converted accelerometer readings by a gain matrix 610 and subtracting (or adding) the results from (or to) the corresponding sampled rotational sensor data 612. For example, the sampled rotational data αy from rotational sensor 502 can be compensated for linear acceleration at block 614 as:

$$\alpha y'=\alpha y-C*A \qquad (4)$$

wherein C is the 1×3 row vector of rotational sensor susceptibility to linear acceleration along each axis given in units/g and A is the calibrated linear acceleration. Similarly, linear acceleration compensation for the sampled rotational data αz from rotational sensor 504 can be provided at block 614. The gain matrices, C, vary between rotational sensors due to manufacturing differences. C may be computed using the average value for many rotational sensors, or it may be custom computed for each rotational sensor.

Like the accelerometer data, the sampled rotational data 612 is then converted from a sampled unit value into a value associated with a rate of angular rotation, e.g., radians/s, at function 616. This conversion step can also include calibration provided by function 618 to compensate the sampled rotational data for, e.g., scale and offset. Conversion/calibration for both αy and αz can be accomplished using, for example, the following equation:

$$\alpha\mathrm{rad}/s=(\alpha'-\mathrm{offset}(T))*\mathrm{scale}+d\mathrm{Offset} \qquad (5)$$

wherein α' refers to the value being converted/calibrated, offset(T) refers to an offset value associated with temperature, scale refers to the conversion factor between the sampled unit value and rad/s, and dOffset refers to a dynamic offset value. Equation (5) may be implemented as a matrix equation in which case all variables are vectors except for scale. In matrix equation form, scale corrects for axis misalignment and rotational offset factors. Each of these variables is discussed in more detail below.

The offset values offset(T) and dOffset can be determined in a number of different ways. When the 3D pointing device 400 is not being rotated in, for example, the y-axis direction, the sensor 502 should output its offset value. However, the offset can be highly affected by temperature, so this offset value will likely vary. Offset temperature calibration may be performed at the factory, in which case the value(s) for offset(T) can be preprogrammed into the handheld device 400 or, alternatively, offset temperature calibration may also be learned dynamically during the lifetime of the device. To accomplish dynamic offset compensation, an input from a temperature sensor 619 is used in rotation calibration function 618 to compute the current value for offset(T). The offset(T) parameter removes the majority of offset bias from the sensor readings. However, negating nearly all cursor drift at zero movement can be useful for producing a high-performance pointing device. Therefore, the additional factor dOffset, can be computed dynamically while the 3D pointing device 400 is in use. The stationary detection function 608 determines when the handheld is most likely stationary and when the offset should be recomputed. Exemplary techniques for implementing stationary detection function 608, as well as other uses therefore, are described below.

An exemplary implementation of dOffset computation employs calibrated sensor outputs which are low-pass filtered. The stationary output detection function 608 provides an indication to rotation calibration function 618 to trigger computation of, for example, the mean of the low-pass filter output. The stationary output detection function 608 can also control when the newly computed mean is factored into the existing value for dOffset. Those skilled in the art will recognize that a multitude of different techniques can be used for computing the new value for dOffset from the existing value of dOffset and the new mean including, but not limited to, simple averaging, low-pass filtering and Kalman filtering. Additionally, those skilled in the art will recognize that numerous variations for offset compensation of the rotational sensors 502 and 504 can be employed. For example, the offset(T) function can have a constant value (e.g., invariant with temperature), more than two offset compensation values can be used and/or only a single offset value can be computed/used for offset compensation.

After conversion/calibration at block 616, the inputs from the rotational sensors 502 and 504 can be further processed to rotate those inputs into an inertial frame of reference, i.e., to compensate for tilt associated with the manner in which the user is holding the 3D pointing device 400, at function 620. Tilt correction is another significant aspect of some exemplary embodiments of the present invention as it is intended to compensate for differences in usage patterns of 3D pointing devices according to the present invention. More specifically, tilt correction according to exemplary embodiments of the present invention is intended to compensate for the fact that users will hold pointing devices in their hands at different x-axis rotational positions, but that the sensing axes of the rotational sensors 502 and 504 in the 3D pointing devices 400 are fixed. It is desirable that cursor translation across display 408 is substantially insensitive to the way in which the user grips the 3D pointing device 400, e.g., rotating the 3D pointing device 400 back and forth in a manner generally corresponding to the horizontal dimension ($x_2$-axis) of the display 508 should result in cursor translation along the $x_2$-axis, while rotating the 3D pointing device up and down in a manner generally corresponding to the vertical dimension ($y_2$-axis) of the display 508 should result in cursor translation along the $y_2$-axis, regardless of the orientation in which the user is holding the 3D pointing device 400.

To better understand the need for tilt compensation according to exemplary embodiments of the present invention, consider the example shown in FIG. 6(*a*). Therein, the user is holding 3D pointing device 400 in an exemplary inertial frame of reference, which can be defined as having an x-axis rotational value of 0 degrees. The inertial frame of reference can, purely as an example, correspond to the orientation illustrated in FIG. 6(*a*) or it can be defined as any other orientation. Rotation of the 3D pointing device 400 in either the y-axis or z-axis directions will be sensed by rotational sensors 502 and 504, respectively. For example, rotation of the 3D pointing device 400 around the z-axis by an amount Δz as shown in FIG. 6(*b*) will result in a corresponding cursor translation Δ$x_2$ in the $x_2$ axis dimension across the display 408 (i.e., the distance between the dotted version of cursor 410 and the undotted version).

If, on the other hand, the user holds the 3D pointing device 400 in a different orientation, e.g., with some amount of x-axis rotation relative to the inertial frame of reference, then the information provided by the sensors 502 and 504 would not (absent tilt compensation) provide an accurate representation of the user's intended interface actions. For example, referring to FIG. 6(*c*), consider a situation wherein the user holds the 3D pointing device 400 with an x-axis rotation of 45 degrees relative to the exemplary inertial frame of reference as illustrated in FIG. 6(*a*). Assuming the same z-axis rotation Δz by a user, the cursor 410 will instead be translated in both the $x_2$-axis direction and the $y_2$-axis direction by as shown in FIG. 6(*d*). This is due to the fact that the sensing axis of rotational sensor 502 is now oriented between the y-axis and the z-axis (because of the orientation of the device in the user's hand). Similarly, the sensing axis of the rotational sensor 504 is also oriented between the y-axis and the z-axis (although in a different quadrant). In order to provide an interface which is transparent to the user in terms of how the 3D pointing device 400 is held, tilt compensation according to exemplary embodiments of the present invention translates the readings output from rotational sensors 502 and 504 back into the inertial frame of reference as part of processing the readings from these sensors into information indicative of rotational motion of the 3D pointing device 400.

According to exemplary embodiments of the present invention, returning to FIG. 5, this can be accomplished by determining the tilt of the 3D pointing device 400 using the inputs y and z received from accelerometer 506 at function 622. More specifically, after the acceleration data is converted and calibrated as described above, it can be low pass filtered at LPF 624 to provide an average acceleration (gravity) value to the tilt determination function 622. Then, tilt θ can be calculated in function 622 as:

$$\theta = \tan^{-1}\left(\frac{y}{z}\right) \tag{7}$$

The value θ can be numerically computed as a tan 2(y,z) to prevent division by zero and give the correct sign. Then, function 620 can perform the rotation R of the converted/calibrated inputs αy and αz using the equation:

$$R = \begin{bmatrix} \cos\theta & \sin\theta \\ -\sin\theta & \cos\theta \end{bmatrix} \cdot \begin{bmatrix} \alpha y \\ \alpha z \end{bmatrix} \tag{8}$$

to rotate the converted/calibrated inputs αy and αz to compensate for the tilt θ. Tilt compensation as described in this exemplary embodiment is a subset of a more general technique for translating sensor readings from the body frame of reference into a user's frame of reference, which techniques are further described in the above-incorporated by reference patent application entitled "3D Pointing Devices with Tilt Compensation and Improved Usability".

Once the calibrated sensor readings have been compensated for linear acceleration, processed into readings indicative of angular rotation of the 3D pointing device 400, and compensated for tilt, post-processing can be performed at blocks 626 and 628. Exemplary post-processing can include compensation for various factors such as human tremor. Although tremor may be removed using several different methods, one way to remove tremor is by using hysteresis. The angular velocity produced by rotation function 620 is integrated to produce an angular position. Hysteresis of a calibrated magnitude is then applied to the angular position. The derivative is taken of the output of the hysteresis block to again yield an angular velocity. The resulting output is then scaled at function 628 (e.g., based on the sampling period) and used to generate a result within the interface, e.g., movement of a cursor 410 on a display 408.

Figure 7:
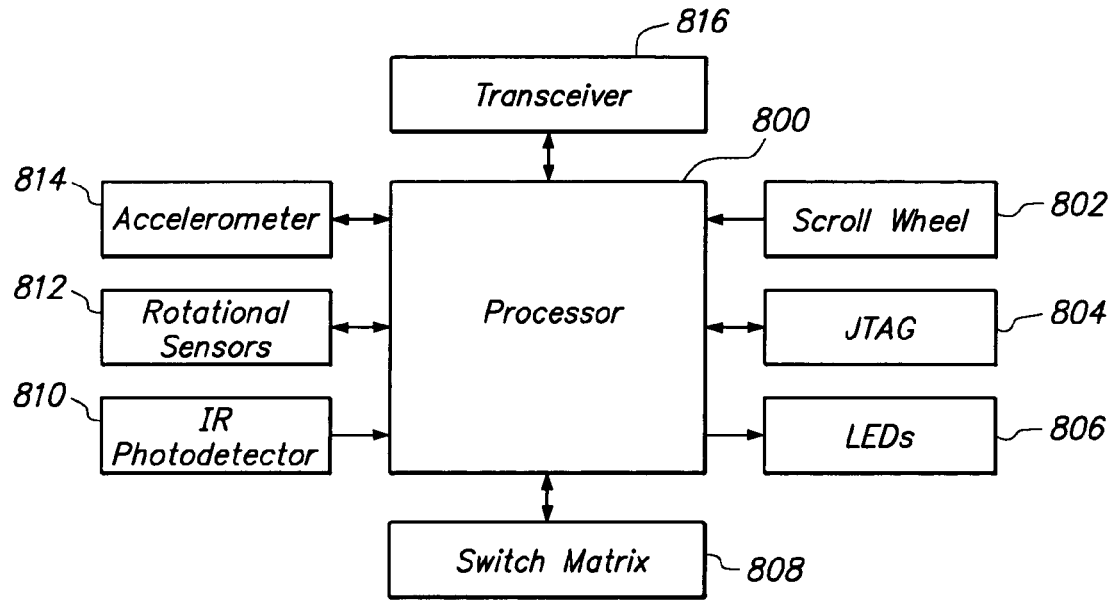
FIG. 7 depicts a hardware architecture of a 3D pointing device according to an exemplary embodiment of the present invention.

Having provided a process description of exemplary 3D pointing devices according to the present invention, FIG. 7 illustrates an exemplary hardware architecture. Therein, a processor 800 communicates with other elements of the 3D pointing device including a scroll wheel 802, JTAG 804, LEDs 806, switch matrix 808, IR photodetector 810, rotational sensors 812, accelerometer 814 and transceiver 816. The scroll wheel 802 is an optional input component which enables a user to provide input to the interface by rotating the scroll wheel 802 clockwise or counterclockwise. JTAG 804 provides the programming and debugging interface to the processor. LEDs 806 provide visual feedback to a user, for example, when a button is pressed. Switch matrix 808 receives inputs, e.g., indications that a button on the 3D pointing device 400 has been depressed or released, that are then passed on to processor 800. The optional IR photodetector 810 can be provided to enable the exemplary 3D pointing device to learn IR codes from other remote controls. Rotational sensors 812 provide readings to processor 800 regarding, e.g., the y-axis and z-axis rotation of the 3D pointing device as described above. Accelerometer 814 provides readings to processor 800 regarding the linear acceleration of the 3D pointing device 400 which can be used as described above, e.g., to perform tilt compensation and to compensate for errors which linear acceleration introduces into the rotational readings generated by rotational sensors 812. Transceiver 816 is used to communicate information to and from 3D pointing device 400, e.g., to the system controller 228 or to a processor associated with a computer. The transceiver 816 can be a wireless transceiver, e.g., operating in accordance with the Bluetooth standards for short-range wireless communication or an infrared transceiver. Alternatively, 3D pointing device 400 can communicate with systems via a wireline connection.

In the exemplary embodiment of FIG. 4, the 3D pointing device 400 includes two rotational sensors 502 and 504, as well as an accelerometer 506. However, according to another exemplary embodiment of the present invention, a 3D pointing device can alternatively include just one rotational sensor, e.g., for measuring angular velocity in the z-axis direction, and an accelerometer. For such an exemplary embodiment, similar functionality to that described above can be provided by using the accelerometer to determine the angular velocity along the axis which is not sensed by the rotational sensor. For example, rotational velocity around the y-axis can be computed using data generated by the accelerometer and calculating:

$$\omega_Y = \frac{\partial \theta_Y}{\partial t} = \frac{\partial}{\partial t} \tan^{-1}\left(\frac{x}{z}\right) \quad (9)$$

In addition, the parasitic acceleration effects that are not measured by a rotational sensor should also be removed. These effects include actual linear acceleration, acceleration measured due to rotational velocity and rotational acceleration, and acceleration due to human tremor.

Stationary detection function 608, mentioned briefly above, can operate to determine whether the 3D pointing device 400 is, for example, either stationary or active (moving). This categorization can be performed in a number of different ways. One way, according to an exemplary embodiment of the present invention, is to compute the variance of the sampled input data of all inputs (x, y, z, αy, αz) over a predetermined window, e.g., every quarter of a second. This variance is then compared with a threshold to classify the 3D pointing device as either stationary or active.

Another stationary detection technique according to exemplary embodiments of the present invention involves transforming the inputs into the frequency domain by, e.g., performing a Fast Fourier Transform (FFT) on the input data. Then, the data can be analyzed using, e.g., peak detection methods, to determine if the 3D pointing device 400 is either stationary or active. Additionally, a third category can be distinguished, specifically the case where a user is holding the 3D pointing device 400 but is not moving it (also referred to herein as the "stable" state. This third category can be distinguished from stationary (not held) and active by detecting the small movement of the 3D pointing device 400 introduced by a user's hand tremor when the 3D pointing device 400 is being held by a user. Peak detection can also be used by stationary detection function 608 to make this determination. Peaks within the range of human tremor frequencies, e.g., nominally 8-12 Hz, will typically exceed the noise floor of the device (experienced when the device is stationary and not held) by approximately 20 dB.

In the foregoing examples, the variances in the frequency domain were sensed within a particular frequency range, however the actual frequency range to be monitored and used to characterize the status of the 3D pointing device 400 may vary. For example, the nominal tremor frequency range may shift based on e.g., the ergonomics and weight of the 3D pointing device 400, e.g., from 8-12 Hz to 4-7 Hz.

Figure 8:
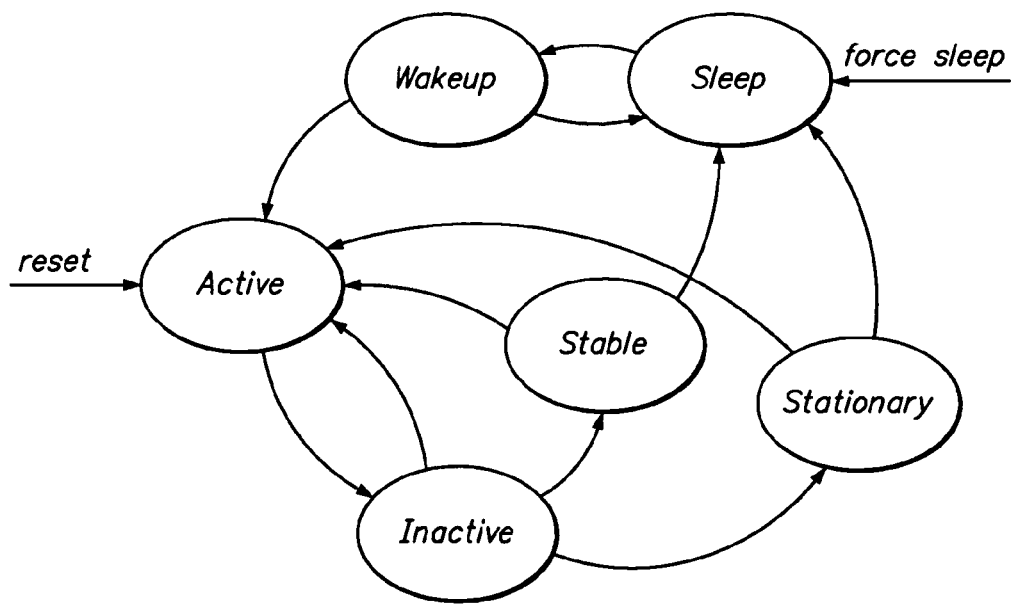
FIG. 8 is a state diagram depicting a stationary detection mechanism according to an exemplary embodiment of the present invention.

According to another exemplary embodiment of the present invention, stationary detection mechanism 608 can include a state machine. An exemplary state machine is shown in FIG. 8. Therein, the ACTIVE state is, in this example, the default state during which the 3D pointing device 400 is moving and being used to, e.g., provide inputs to a user interface. The 3D pointing device 400 can enter the ACTIVE state on power-up of the device as indicated by the reset input. If the 3D pointing device 400 stops moving, it may then enter the INACTIVE state. The various state transitions illustrated in FIG. 8 can be triggered by any of a number of different criteria including, but not limited to, data output from one or both of the rotational sensors 502 and 504, data output from the accelerometer 506, time domain data, frequency domain data or any combination thereof. State transition conditions will be generically referred to herein using the convention "Condition$_{stateA \rightarrow stateB}$". For example, the 3D pointing device 400 will transition from the ACTIVE state to the INACTIVE state when condition$_{active \rightarrow inactive}$ occurs. For the sole purpose of illustration, consider that condition$_{active \rightarrow inactive}$ can, in an exemplary 3D pointing device 400, occur when mean and/or standard deviation values from both the rotational sensor(s) and the accelerometer fall below first predetermined threshold values for a first predetermined time period. When in the ACTIVE state, data received from the motion sensors (e.g., rotational sensor(s) and/or accelerometer) can be separated into first data associated with intentional movement introduced by a user and second data associated with unintentional movement introduced by a user (tremor) using one or more processing techniques such as linear filtering, Kalman filtering, Kalman smoothing, state-space estimation, Expectation-Maximization, or other model-based techniques. The first data can then be further processed to generate an output associated with the intended movement of the handheld device (e.g., to support cursor movement) while the second data can be used as tremor input for, e.g., user identification, as described in more detail below.

State transitions can be determined by a number of different conditions based upon the interpreted sensor outputs. Exemplary condition metrics include the variance of the interpreted signals over a time window, the threshold between a reference value and the interpreted signal over a time window, the threshold between a reference value and the filtered interpreted signal over a time window, and the threshold between a reference value and the interpreted signal from a start time can be used to determine state transitions. All, or any combination, of these condition metrics can be used to trigger state transitions. Alternatively, other metrics can also be used. According to one exemplary embodiment of the present invention, a transition from the INACTIVE state to the ACTIVE state occurs either when (1) a mean value of sensor output(s) over a time window is greater than predetermined threshold(s) or (2) a variance of values of sensor output(s) over a time window is greater than predetermined threshold(s) or (3) an instantaneous delta between sensor values is greater than a predetermined threshold.

The INACTIVE state enables the stationary detection mechanism 608 to distinguish between brief pauses during which the 3D pointing device 400 is still being used, e.g., on the order of a tenth of a second, and an actual transition to either a stable or stationary condition. This protects against the functions which are performed during the STABLE and STATIONARY states, described below, from inadvertently being performed when the 3D pointing device is being used. The 3D pointing device 400 will transition back to the ACTIVE state when condition$_{inactive \rightarrow active}$ occurs, e.g., if the 3D pointing device 400 starts moving again such that the measured outputs from the rotational sensor(s) and the accelerometer exceeds the first threshold before a second predetermined time period in the INACTIVE state elapses.

The 3D pointing device 400 will transition to either the STABLE state or the STATIONARY state after the second predetermined time period elapses. As mentioned earlier, the STABLE state reflects the characterization of the 3D pointing device 400 as being held by a person but being substantially unmoving, while the STATIONARY state reflects a characterization of the 3D pointing device as not being held by a person. Thus, an exemplary state machine according to the present invention can provide for a transition to the STABLE state after the second predetermined time period has elapsed if minimal movement associated with hand tremor is present or, otherwise, transition to the STATIONARY state.

The STABLE and STATIONARY states define times during which the 3D pointing device 400 can perform various functions. For example, since the STABLE state is intended to reflect times when the user is holding the 3D pointing device 400 but is not moving it, the device can record the movement of the 3D pointing device 400 when it is in the STABLE state e.g., by storing outputs from the rotational sensor(s) and/or the accelerometer while in this state. These stored measurements can be used to determine a tremor pattern associated with a particular user or users as described below. Likewise, when in the STATIONARY state, the 3D pointing device 400 can take readings from the rotational sensors and/or the accelerometer for use in compensating for offset as described above.

If the 3D pointing device 400 starts to move while in either the STABLE or STATIONARY state, this can trigger a return to the ACTIVE state. Otherwise, after measurements are taken, the device can transition to the SLEEP state. While in the sleep state, the device can enter a power down mode wherein power consumption of the 3D pointing device is reduced and, e.g., the sampling rate of the rotational sensors and/or the accelerometer is also reduced. The SLEEP state can also be entered via an external command so that the user or another device can command the 3D pointing device 400 to enter the SLEEP state.

Upon receipt of another command, or if the 3D pointing device 400 begins to move, the device can transition from the SLEEP state to the WAKEUP state. Like the INACTIVE state, the WAKEUP state provides an opportunity for the device to confirm that a transition to the ACTIVE state is justified, e.g., that the 3D pointing device 400 was not inadvertently jostled.

The conditions for state transitions may be symmetrical or may differ. Thus, the threshold associated with the condition$_{active \rightarrow inactive}$ may be the same as (or different from) the threshold(s) associated with the condition$_{inactive \rightarrow active}$. This enables 3D pointing devices according to the present invention to more accurately capture user input. For example, exemplary embodiments which include a state machine implementation allow, among other things, for the threshold for transition into a stationary condition to be different than the threshold for the transition out of a stationary condition.

Entering or leaving a state can be used to trigger other device functions as well. For example, the user interface can be powered up based a transition from any state to the ACTIVE state. Conversely, the 3D pointing device and/or the user interface can be turned off (or enter a sleep mode) when the 3D pointing device transitions from ACTIVE or STABLE to STATIONARY or INACTIVE. Alternatively, the cursor 410 can be displayed or removed from the screen based on the transition from or to the stationary state of the 3D pointing device 400.

As mentioned above, the period of time during which the handheld device is in the STABLE state can, for example, be used to memorize tremor data associated with a particular user. Typically, each user will exhibit a different tremor pattern. According to exemplary embodiments of the present invention, this property of user tremor can be used to identify which user is currently holding the handheld device without requiring any other action on the part of the user (e.g., entering a password). For example, a user's tremor pattern can be memorized by the handheld or the system (e.g., either stored in the 3D pointing device 400 or transmitted to the system) during an initialization procedure wherein the user is requested to hold the 3D pointing device as steadily as possible for, e.g., 10 seconds.

This pattern can be used as the user's unique (or quasi-unique) signature to perform a variety of user interface functions. For example, the user interface and/or the handheld device can identify the user from a group of users, e.g., a family, by comparing a current tremor pattern with those stored in memory. The identification can then be used, for example, to retrieve preference settings associated with the identified user. For example, if the 3D pointing device is used in conjunction with the media systems described in the above-incorporated by reference patent application, then the media selection item display preferences associated with that user can be activated after the system recognizes the user via tremor pattern comparison. System security can also be implemented using tremor recognition, e.g., access to the system may be forbidden or restricted based on the user identification performed after a user picks up the 3D pointing device 400.

Figure 9:
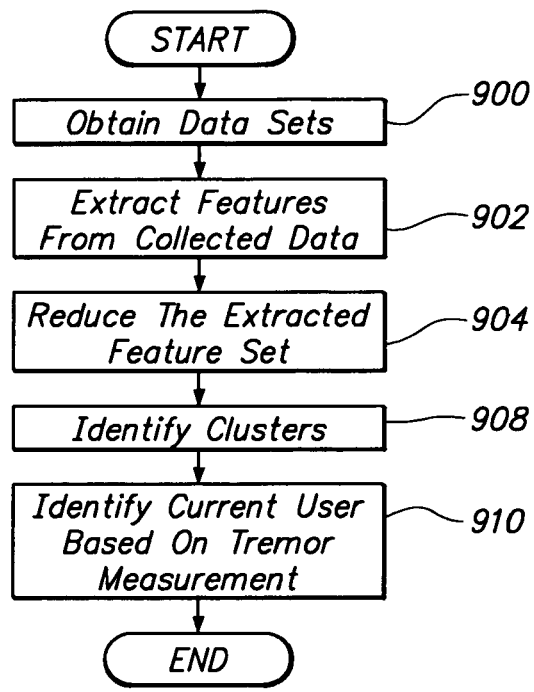
FIG. 9 is a flow chart illustrating a method of identifying a user based on detected hand tremor of a handheld device according to an exemplary embodiment of the present invention.

A number of different approaches can be taken to implement schemes for tremor pattern detection, classification and storage according to the present invention. One exemplary embodiment will now be described with respect to FIGS. 9-12. An overall method for classifying tremor patterns is depicted in the flowchart of FIG. 9. Therein, data sets are collected from a plurality of users at step 900. Data set collection can be part of a training/initialization process, wherein a user is asked to hold the device without introducing intentional motion for a predetermined period of time (e.g., 5-15 seconds) or can be performed "on-the-fly" during use of the handheld device. Moreover, data collection can be performed while holding the handheld device in a predetermined orientation. Some purely exemplary frequency spectra data, shown in FIGS. 10(*a*)-10(*d*), was collected for a particular user holding a 3D pointing device 400 in four different orientations.

Returning to FIG. 9, the collected data can then be processed in order to identify classes which are each associated with different users of the handheld device 400. For example, one or more feature sets can be extracted from each set of collected data for use in the classification process at step 902. The particular feature set or feature sets which are selected for use in step 902 is chosen to provide good class distinction for tremor data and may vary depending upon implementation parameters associated with the user identification via tremor process including, for example, the number of users to be distinguished in the classification pool, the amount and type of training data to be collected at step 900, device characteristics, state information as described above e.g., with respect to FIG. 8 and associated Bayesian user information (e.g. time-of-day). An exemplary list of feature sets which can be employed at step 902 are provided below as Table 1 below.

TABLE 1

| | |
|---|---|
| Time-Domain | AR coefficients (e.g. RPLR or iterative INVFREQZ method) Normalized autocorrelation lags, AR coefficients (e.g. RPLR), Keenan, Tsay, or Subba Rao tests, features of the pure distribution of the time series, time reversal invariance, asymmetric decay of the autocorrelation function |
| Frequency-Domain | PSD of rotational sensors - features (e.g. peak frequencies, moments), PSD coefficients PSD of accelerometers - features (e.g. peak frequencies, moments), PSD coefficients Cross-spectral analysis of rotational sensor data with accelerometer data |
| Higher-Order Statistics | HOS (Bispectrum, trispectrum) - exploit non-gaussianity of tremor Hinich statistical tests Volterra series modeling |
| Time-Frequency Domain | Parameters extracted from STFT, Wigner-Ville and/or (Choi-Williams) TF distributions. |
| Time-Scale Domain | DWT - Discrete Wavelet Transform MODWT - Maximum Overlap Transform (cyclic-invariant) CWT - Complex Wavelet Transform (shift-invariant) |
| Other Transforms | Periodicity Transforms (e.g. small-to-large, m-best, etc.) Cyclic Spectra |
| Other Measures | Chaotic measures (e.g. Lyapunov exponents, fractal dimension, correlation dimension) |

Information regarding some of these feature sets and corresponding tests can be found in the article by J. Jakubowski, K. Kwiatos, A. Chwaleba, S. Osowski, "*Higher Order Statistics and Neural Network For Tremor Recognition,*" IEEE Transactions on Biomedical Engineering, vol. 49, no. 2, pp. 152-159, IEEE, February 2002, the disclosure of which is incorporated here by reference. According to one purely exemplary embodiment of the present invention, described in more detail below, low frequency spectra from a power spectral density (PSD) of the collected data was used as the feature set at step 902. In addition to the domains, transforms etc., listed above, the features sets may also vary based on the number and types of sensors available in the handheld device for which tremor detection/identification is to be employed. For example, in the handheld, 3D pointing device 400 described in earlier exemplary embodiments, tremor data can be collected from one or both of the rotational sensors, the accelerometer, or any combination thereof.

After extracting the feature set from the collected data, the feature set can be reduced at step 904. More specifically, the feature set can be reduced at step 904 to the set of features which best represent the feature set for purposes of differentiating between classes (users). For example, the DC values of user tremor data may be omitted from the reduced feature set, whereas the 9 Hz values of user tremor data may be included in the reduced feature set, since the latter would be expected to be more useful in distinguishing between different user's hand tremors. The reduced feature set can, for example, be a Most Expressive Feature (MEF) set which is determined using a Principal Component Analysis (PCA) algorithm. The PCA algorithm employs a singular value decomposition of the features set to automatically find an appropriate set of basis vectors that best expresses the feature vectors (e.g., in the sense of minimum mean-squared error (MMSE)). An example for applying the PCA technique can be found in "Eigenspace-Based Recognition of Faces: Comparisons and a New Approach," authored by P. Navarrete and J. Ruiz-del Solar, Image Analysis and Processing, 2001, the disclosure of which is incorporated here by reference.

The reduced feature sets can then be used to identify clusters at step 908, which can be performed using supervised learning i.e., wherein the process operates based on a priori knowledge of which individual user contributed which data set or unsupervised learning, i.e., wherein the process does not have any a priori information. Various techniques can be applied to determine clusters associated with tremor data according to exemplary embodiments of the present invention, including, for example, K-means clustering and RBF neural net classification. Once the clusters are identified, then estimated statistics associated with the identified clusters (e.g., mean and/or covariance) can be used to distinguish new feature vectors as lying within certain clusters or outside of certain clusters, i.e., to identify a user who is currently holding the handheld device 400 based on current sensor outputs, at step 910. The learning method can be enhanced via use of the sensor state information (described above, e.g., with respect to FIG. 8) by refining clusters centers during sensor operation, after initial user/cluster instantiation. In this way, the maximum amount of available data is used to refine clusters (in a supervised manner), to support further unsupervised learning.

Figure 11:
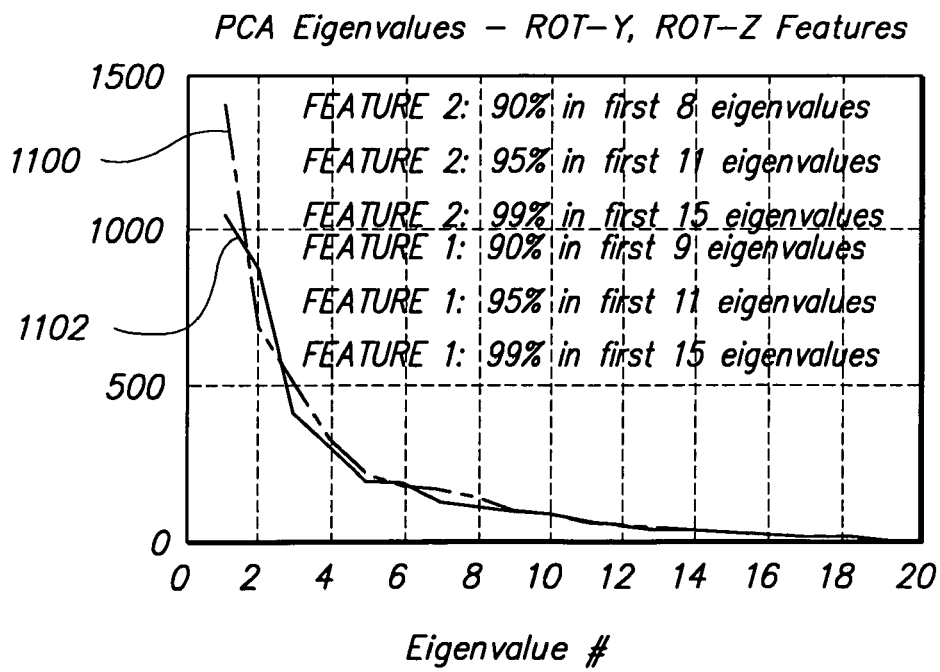
FIG. 11 is a graph plotting eigenvalues associated with a method for identifying a user based on hand tremor according to an exemplary embodiment of the present invention.
Figure 10A:
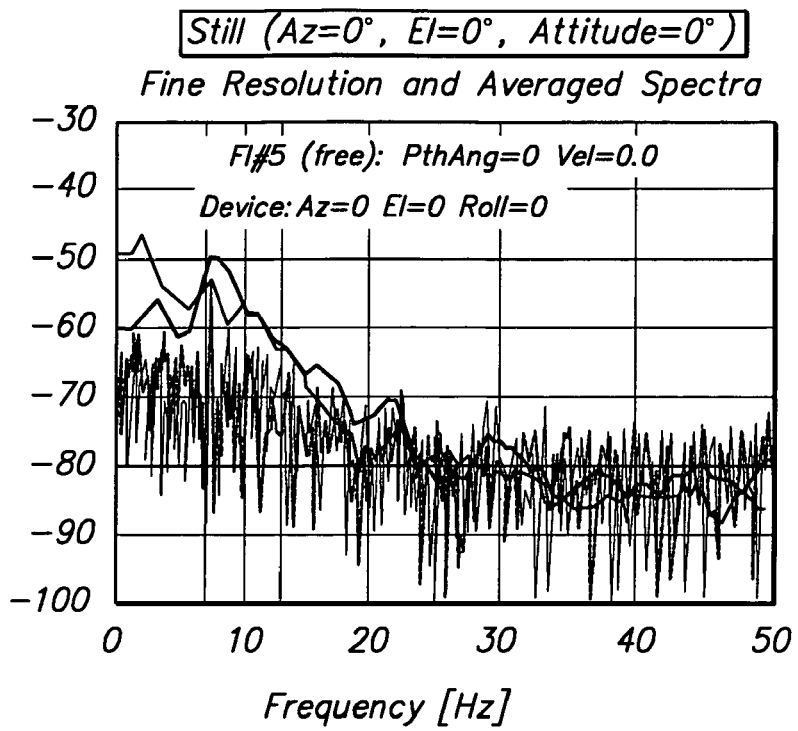
FIGS. 10(a)-10(d) are plots of frequency domain tremor data collected as part of a test of an exemplary method and device for identifying a user based on hand tremor according to an exemplary embodiment of the present invention.
Figure 10B:
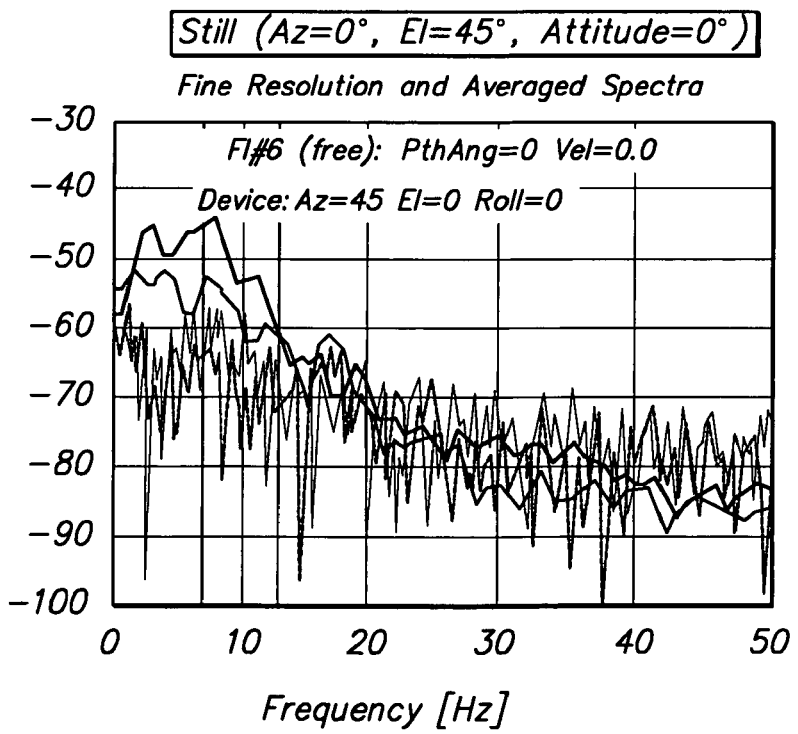
Figure 10C:
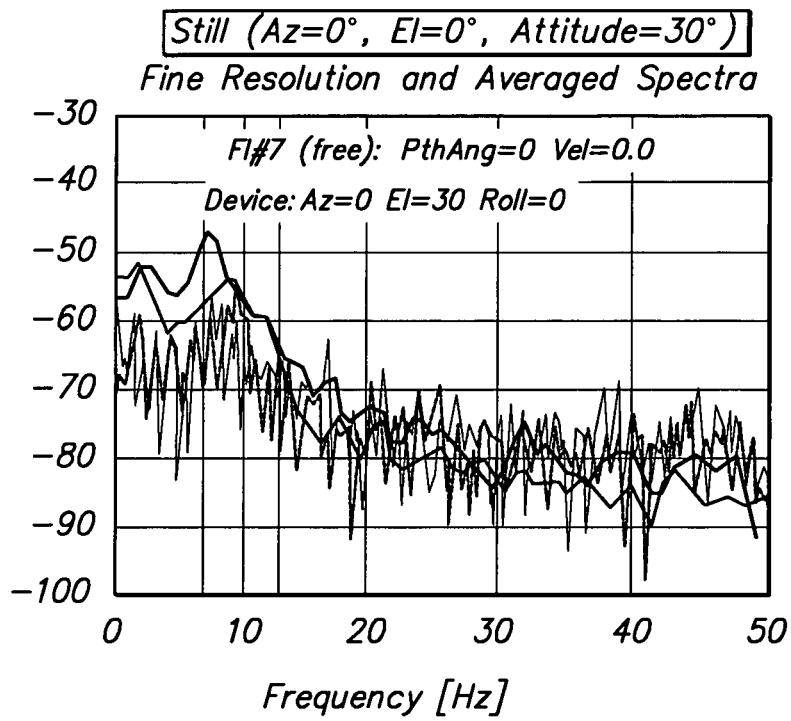
Figure 10D:
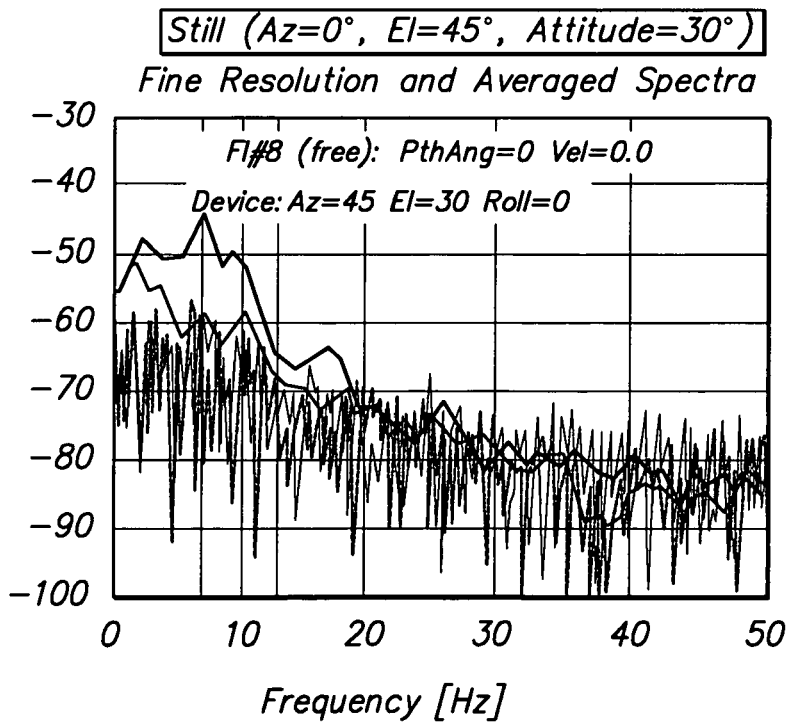

To test the afore-described exemplary techniques for identifying users based on detected hand tremor, data sets associated with four other users (in addition to the data illustrated in FIGS. 10(a)-10(d)) were collected and analyzed in the general manner described above with respect to the flowchart of FIG. 9 to demonstrate that hand tremor analysis can be used to distinguish between/identify different users. Two of the data sets were collected from the same person holding the handheld device, while the other three data sets were collected from different people holding the handheld device. In this test, data was collected from both of the rotational sensors 812 for each of the five data sets at step 900. Each of the data sets was processed to have zero-mean and unit variance. For this exemplary test, low-frequency spectra from a PSD estimate (e.g., peak frequencies) were used for the feature set extraction, averaged over the data collection time, at step 902. More specifically, 256 point FFTs were used averaged with a 75% overlap over N=2048 points within a frequency range of 0-30 Hz. The extracted feature set was reduced from a 38×20 matrix to a 20×20 matrix using the PCA algorithm, which correctly recognized that certain eigenvectors associated with the extracted feature set are less expressive than others and can be discarded. FIG. 11 illustrates eigenvalues generated as part of step 904 in this example. Therein, line 1100 depicts eigenvalues associated with feature set 2 (data collected from rotational sensor 504, z-azis rotation) and line 1102 depicts eigenvalues associated with feature set 1 (data collected from rotational sensor 502, y-axis rotation).

Figure 12:
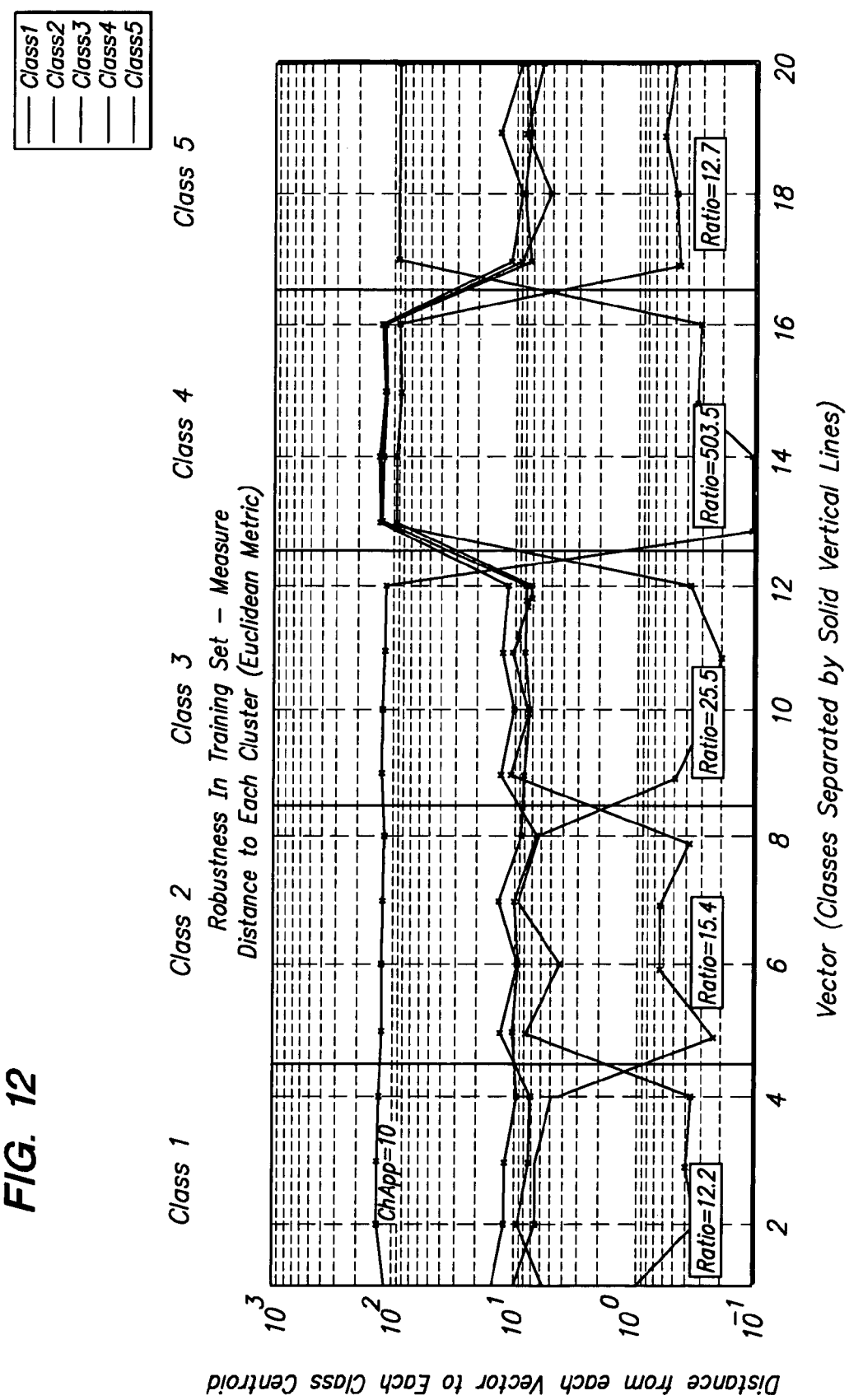
FIG. 12 is a graph illustrating class separation results associated with an exemplary method for identifying users based on hand tremor according to an exemplary embodiment of the present invention.

In this test case, the clustering step was performed based on the a priori knowledge (supervised learning) of which user generated which data set. In an actual implementation, it is likely that an automated clustering technique, e.g., one of those described above, would be employed at step 906. For this purely exemplary test, clusters were identified separately for data received from the rotational sensor 502 and 504 to define two class centroids associated with each data set. Then, the sum of the distances (Euclidean in this example) between each vector in the data sets and the two class centroids was calculated. The results of this process are shown in FIG. 12. Therein, the x-axis represents the reduced data set vectors, the y-axis represents distance and the vertical lines partition distances to different class (user) centroids. It can be seen that within each partition the associated class' vector-to-centroid distance is significantly lower than the other classes' vector-to-centroid distance, illustrating good class separation and an ability to distinguish/identify users based on the hand tremor that they induce in a handheld device.

Some specific selections of, e.g., feature sets, etc. were made to perform the illustrated test, however these selections are purely illustrative as mentioned herein.

A number of variations can be employed according to exemplary embodiments of the present invention. For example, once the clusters are identified at step 908, a cluster discrimination step can be performed in order to accentuate the discriminating feature(s) of each cluster. A cluster discriminant operates to apply a transformation matrix to the data which provides a minimum grouping within sets, and a maximum distance between sets. Given a matrix which describes the overall covariance, and another which describes the sum of the covariances of each of the clusters, the linear discriminant's task is to derive a linear transformation which simultaneously maximizes the distances between classes and minimizes the within-class scatter. Although a number of discriminants are known in the general field of pattern recognition, for example the Fisher Linear Discriminant (FLD), not all are likely to be suitable to the specific problem of identifying users based on hand tremor as described herein. One specific discriminant which was used in the foregoing text example, is known as the EFM-1 discriminant and is described in the article entitled "Enhanced Fisher Linear Discriminant Models for Face Recognition", authored by C. Liu and H. Wechsler, Proc. 14$^{th}$ International Conference on Pattern Recognition, Queensland Australia, Aug., 17-20, 1998, the disclosure of which is incorporated here by reference.

Moreover, although the foregoing test was performed using a handheld pointing device in accordance with earlier described exemplary embodiments of the present invention, tremor-based identification of users is not so limited. In fact, tremor-based identification can be employed in any other type of 3D pointing device having any type of motion sensor or sensors (including gyroscopes) from which tremor data can be generated. Further, tremor-based identification in accordance with the present invention is also not limited to pointing devices, but can be employed in any handheld device, e.g., cell phones, PDAs, etc., which incorporate one or more motion sensors or which have some other mechanism for measuring hand tremor associated therewith. A training period may be employed to perform, e.g., steps 900-908, subsequent to which a handheld device can perform a method which simply gathers data associated with the hand tremor of a current user and compares that data with the previously established user classes to identify the current user. This identity information can then be used in a number of different applications, examples of which are mentioned above.

For example, the identity of the user (as recognized by tremor-based recognition or via another identification technique) can be used to interpret gestures made by that user to signal commands to a user interface, e.g., that of the above-incorporated by reference patent application. For example, in a gesture based command system wherein patterns of movement over time are associated with specific interface commands, different users may employ somewhat different patterns of movement over time of the handheld to initiate the same interface command (much like different people have different handwriting styles). The ability to provide for user identification can then be mapped to the different gesture patterns, e.g., stored in the handheld or in the system, such that the system as a whole correctly identifies each pattern of movement over time as the command gesture intended by the user.

The above-described exemplary embodiments are intended to be illustrative in all respects, rather than restrictive, of the present invention. Thus the present invention is capable of many variations in detailed implementation that can be derived from the description contained herein by a person skilled in the art. For example, although the foregoing exemplary embodiments describe, among other things, the use of inertial sensors to detect movement of a device, other types of sensors (e.g., ultrasound, magnetic or optical) can be used instead of, or in addition to, inertial sensors in conjunction with the afore-described signal processing. All such variations and modifications are considered to be within the scope and spirit of the present invention as defined by the following claims. No element, act, or instruction used in the description of the present application should be construed as critical or essential to the invention unless explicitly described as such. Also, as used herein, the article "a" is intended to include one or more items.

The invention claimed is:

1. A handheld, pointing device comprising:
a first rotational sensor for determining rotation of said pointing device about a first axis and generating a first rotational output associated therewith;
a second rotational sensor for determining rotation of said pointing device about a second axis and generating a second rotational output associated therewith;
an accelerometer for determining an acceleration of said pointing device and outputting an acceleration output associated therewith; and
a processing unit for receiving said first and second rotational outputs and said acceleration output and for:
(a) establishing, during a training period, a plurality of hand tremor classes each of which is associated with a user by processing training data derived from at least one of said first and second rotational outputs and said acceleration output while said user is holding said pointing device without intentional movement; and
(b) determining, subsequent to said training period, an identity of a current user of said pointing device by comparing data derived from at least one of a current first rotational output, a current second rotational output and a current acceleration output to said plurality of hand tremor classes established during said training period.

2. The pointing device of claim 1, wherein said first rotational sensor further comprises:
a first resonating mass attached to a first frame, wherein said first resonating mass in said first rotational sensor resonates along said first axis;
wherein displacement of said first resonating mass along said first axis is measured by said first rotational sensor using the Coriolis acceleration effect to generate said first rotational output.

3. The pointing device of claim 2, wherein said second rotational sensor further comprises:
a second resonating mass attached to a second frame, wherein said second resonating mass in said second rotational sensor resonates along said second axis;
wherein displacement of said second resonating mass along said second axis is measured by said second rotational sensor using the Coriolis acceleration effect to generate said second rotational output.

4. A handheld device comprising:
at least one motion sensor capable of generating data associated with movement of said handheld device; and
a processing unit for detecting hand tremor data based on said movement data and for identifying a user based on said hand tremor data, wherein said processing unit performs a pattern recognition technique adapted to distinguish between hand tremors of different users to identify said user.

5. The handheld device of claim 4, wherein said at least one motion sensor includes at least one of: a rotational sensor, a gyroscope, an accelerometer, an inertial sensor, a magnetic sensor, an optical sensor and a camera.

6. The handheld device of claim 4, wherein said processing unit detects said hand tremor data in a frequency domain.

7. The handheld device of claim 4, wherein said processing unit detects said hand tremor data in a time domain.

8. The handheld device of claim 4, wherein said processing unit performs a pattern recognition technique adapted to distinguish between hand tremors of different users to identify said user.

9. The handheld device of claim 4, wherein said processing unit performs a training operation wherein data associated with different users holding said handheld device without introducing intentional movement thereto is recorded and processed.

10. The handheld device of claim 4, wherein said handheld device is a 3D pointing device.

11. A handheld device comprising:
means for generating data associated with movement of said handheld device; and
means for detecting hand tremor data based on said movement data and for identifying a user based on said hand tremor data, wherein said processing unit performs a pattern recognition technique adapted to distinguish between hand tremors of different users to identify said user.

12. A method for operating a handheld device using hand tremor as an input thereto, the method comprising the steps of:
(a) training said handheld device by having a plurality of users each hold said handheld device for a training period;
(b) detecting movement of said handheld device during each training period;
(c) establishing, based on said training periods, a plurality of hand tremor classes each of which is associated with one of said plurality of users, by processing data derived from said detected movement for a respective training period; and
(d) determining, subsequent to said training period, an identity of a current user of said handheld device by comparing data derived from current movement of said handheld device with said plurality of hand tremor classes.

13. The method of claim 12, wherein said training period is variable as between said plurality of users.

14. The method of claim 12, wherein said users hold said handheld device without intentional movement thereof during said training periods.

15. The method of claim 12, wherein said users intentionally move said handheld device during said training periods.

16. The method of claim 12, further comprising the step of:
entering an identification of said user during said training period into a user interface associated with said handheld device; and
associating said identification with a corresponding hand tremor class.

17. The handheld device of claim 11, wherein means for generating data associated with movement of said handheld device includes at least one of: a rotational sensor, a gyroscope, an accelerometer, an inertial sensor, a magnetic sensor, an optical sensor and a camera.

18. The handheld device of claim 11, wherein said means for detecting detects said hand tremor data in a frequency domain.

19. The handheld device of claim 11, wherein said means for detecting detects said hand tremor data in a time domain.

20. The handheld device of claim 11, wherein said means for detecting also performs a training operation wherein data associated with different users holding said handheld device without introducing intentional movement thereto is recorded and processed.

21. The handheld device of claim 11, wherein said handheld device is a free space pointing device.

22. The handheld device of claim 11, wherein said pattern recognition technique includes one of supervised learning and unsupervised learning.

23. The handheld device of claim 11, wherein said pattern recognition technique involves comparing a current tremor pattern with those stored in a memory.

24. The handheld device of claim 4, wherein said pattern recognition technique includes one of supervised learning and unsupervised learning.

25. The handheld device of claim 4, wherein said pattern recognition technique involves comparing a current tremor pattern with those stored in a memory.

26. A handheld device comprising:
at least one motion sensor capable of generating data associated with movement of said handheld device; and
a processing unit for detecting hand tremor data based on said movement data and for identifying a user based on said hand tremor data, wherein said processing unit performs a training operation wherein data associated with different users holding said handheld device without introducing intentional movement thereto is recorded and processed.

27. The handheld device of claim 26, wherein said at least one motion sensor includes at least one of: a rotational sensor, a gyroscope, an accelerometer, an inertial sensor, a magnetic sensor, an optical sensor and a camera.

28. The handheld device of claim 26, wherein said processing unit detects said hand tremor data in a frequency domain.

29. The handheld device of claim 26, wherein said processing unit detects said hand tremor data in a time domain.

30. The handheld device of claim 26, wherein said processing unit performs a pattern recognition technique adapted to distinguish between hand tremors of different users to identify said user.

31. The handheld device of claim 26, wherein said handheld device is a free space pointing device.

32. A system including a handheld device, said system comprising:
   at least one motion sensor capable of generating data associated with movement of said handheld device; and
   a processing unit for detecting hand tremor data based on said movement data and for identifying a user based on said hand tremor data, wherein said processing unit performs a training operation wherein data associated with different users holding said handheld device without introducing intentional movement thereto is recorded and processed.

33. The system of claim 32, wherein said at least one motion sensor includes at least one of: a rotational sensor, a gyroscope, an accelerometer, an inertial sensor, a magnetic sensor, an optical sensor and a camera.

34. The system of claim 32, wherein said processing unit detects said hand tremor data in a frequency domain.

35. The system of claim 32, wherein said processing unit detects said hand tremor data in a time domain.

36. The system of claim 32, wherein said processing unit performs a pattern recognition technique adapted to distinguish between hand tremors of different users to identify said user.

37. The system of claim 26, wherein said handheld device is a free space pointing device.

38. The system of claim 26, wherein said at least one motion sensor is disposed within said handheld device.

39. The system of claim 26, wherein said processing unit is disposed within said handheld device.

40. The system of claim 26, wherein said processing unit is disposed within said system and said movement data is communicated from said handheld device to system for processing by said processing unit.

41. The system of claim 26 further comprising:
   a set-top box in communication with said handheld device.

42. A system, including handheld device, comprising:
   at least one motion sensor capable of generating data associated with movement of said handheld device; and
   a processing unit for detecting hand tremor data based on said movement data and for identifying a user based on said hand tremor data, wherein said processing unit performs a pattern recognition technique adapted to distinguish between hand tremors of different users to identify said user.

43. The system of claim 42, wherein said at least one motion sensor includes at least one of: a rotational sensor, a gyroscope, an accelerometer, an inertial sensor, a magnetic sensor, an optical sensor and a camera.

44. The system of claim 42, wherein said processing unit detects said hand tremor data in a frequency domain.

45. The system of claim 42, wherein said processing unit detects said hand tremor data in a time domain.

46. The system of claim 42, wherein said processing unit performs a training operation wherein data associated with different users holding said handheld device without introducing intentional movement thereto is recorded and processed.

47. The system of claim 42, wherein said handheld device is a free space pointing device.

48. The system of claim 42, wherein said at least one motion sensor is disposed within said handheld device.

49. The system of claim 42, wherein said processing unit is disposed within said handheld device.

50. The system of claim 42, wherein said processing unit is disposed within said system and said movement data is communicated from said handheld device to system for processing by said processing unit.

51. The system of claim 42 further comprising:
   a set-top box in communication with said handheld device.

52. The system of claim 42, wherein said pattern recognition technique includes one of supervised learning and unsupervised learning.

53. The system of claim 42, wherein said pattern recognition technique involves comparing a current tremor pattern with those stored in a memory.

54. A method comprising:
   generating data associated with movement of a handheld device;
   detecting hand tremor data based on said movement data; and
   identifying a user based on said hand tremor data by performing a pattern recognition technique adapted to distinguish between hand tremors of different users.

55. The method of claim 54, wherein said step of generating data uses at least one of: a rotational sensor, a gyroscope, an accelerometer, an inertial sensor, a magnetic sensor, an optical sensor and a camera.

56. The method of claim 54, wherein step of detecting hand tremor detects said hand tremor data in a frequency domain.

57. The method of claim 54, wherein step of detecting hand tremor detects said hand tremor data in a time domain.

58. The method of claim 54, further comprising:
   performing a training operation wherein data associated with different users holding said handheld device without introducing intentional movement thereto is recorded and processed.

59. The method of claim 54, wherein said handheld device is a free space pointing device.

60. The method of claim 54, wherein said step of generating data is performed within said handheld device.

61. The method of claim 54, wherein at least one of said steps of detecting and identifying are performed within said handheld device.

62. The method of claim 54, further comprising the step of:
   communicating said data associated with said movement of said handheld device from said handheld device to another device,
   wherein at least one of said steps of detecting and identifying are performed within said another device.

63. The method of claim 62 wherein said another device is a set-top box.

64. The system of claim 54, wherein said pattern recognition technique includes one of supervised learning and unsupervised learning.

65. The method of claim 54, wherein said pattern recognition technique involves comparing a current tremor pattern with those stored in a memory.

66. A method comprising:
   performing a training operation wherein data associated with different users holding a handheld device without introducing intentional movement thereto is recorded and processed;
   generating data associated with movement of a handheld device;
   detecting hand tremor data based on said movement data; and
   identifying a user based on said hand tremor data.

67. The method of claim 66, wherein said step of generating data uses at least one of: a rotational sensor, a gyroscope, an accelerometer, an inertial sensor, a magnetic sensor, an optical sensor and a camera.

68. The method of claim 66, wherein step of detecting hand tremor detects said hand tremor data in a frequency domain.

69. The method of claim 66, wherein step of detecting hand tremor detects said hand tremor data in a time domain.

70. The method of claim 66, further comprising:
performing a pattern recognition technique adapted to distinguish between hand tremors of different users.

71. The method of claim 66, wherein said handheld device is a free space pointing device.

72. The method of claim 66, wherein said step of generating data is performed within said handheld device.

73. The method of claim 66, wherein at least one of said steps of detecting and identifying are performed within said handheld device.

74. The method of claim 66, further comprising the step of:
communicating said data associated with said movement of said handheld device from said handheld device to another device,
wherein at least one of said steps of detecting and identifying are performed within said another device.

75. The method of claim 74 wherein said another device is a set-top box.

76. The system of claim 70, wherein said pattern recognition technique includes one of supervised learning and unsupervised learning.

77. The method of claim 70, wherein said pattern recognition technique involves comparing a current tremor pattern with those stored in a memory.

* * * * *

UNITED STATES PATENT AND TRADEMARK OFFICE
CERTIFICATE OF CORRECTION

PATENT NO. : 7,236,156 B2  
APPLICATION NO. : 11/119688  
DATED : June 26, 2007  
INVENTOR(S) : Matthew Liberty et al.

Page 1 of 2

It is certified that error appears in the above-identified patent and that said Letters Patent is hereby corrected as shown below:

Title page, col. 2, under OTHER PUBLICATIONS, change "Navarrete, P., et al., "Eigensapce-based" to --Navarrete, P., et al., "Eigenspace-based--.

In the Specification:

Col. 1, line 19, after "Usability"," insert --and--.

Col. 3, line 29, change "processor" to --process--.

Col. 5, line 13, change "4" to --3--; line 25, change "flow chart" to --flowchart--; and line 60, delete "of" (third occurrence).

Col. 6, line 67, after "pointing" insert --device 400--.

Col. 7, line 12, change "devices" to --device--; line 15, after "device" insert --400--; and line 56, change "ADXRS150s" to --ADXRS150--.

Col. 8, line 2, change "devices" to --device--; line 9, after "device" insert --400--; line 18, change "handheld" to --3D pointing--; line 27, before "device" insert --3D pointing--; line 28, before "device" insert --3D pointing--; line 35, change "devices" to --device 400--; line 44, after "device" insert --400--; line 45, delete "a"; and line 47, after "device," insert --400--.

Col. 9, line 16, delete "an".

Col. 10, line 5, after "compensate" insert --for--; line 28, change "handheld" to --3D pointing--; line 32, after "in" insert --the--; and line 40, change "handheld" to --3D pointing device 400--.

Col. 11, line 11, change "devices" to --device--; and line 51, delete "by".

Signed and Sealed this  
Eleventh Day of June, 2013

Teresa Stanek Rea  
*Acting Director of the United States Patent and Trademark Office*

CERTIFICATE OF CORRECTION (continued)
U.S. Pat. No. 7,236,156 B2

Col. 12, line 51, after "device" insert --400--; line 64, after "device" insert --400--; and line 67, after "device" insert --400--.

Col. 15, line 6, after "device" insert --400--; line 45, change "sleep" to --SLEEP--; and line 47, after "device" insert --400--.

Col. 16, line 6, after "based" insert --on--; line 7, after "device" insert --400--; line 9, after "device" insert --400--; line 12, change "stationary" to --STATIONARY--; line 15, change "handheld device" to --3D pointing device 400--; line 20, change "handheld device" to --3D pointing device 400--; line 23, after "handheld" insert --device--; line 26, after "device" insert --400--; line 35, after "device" insert --400--; and line 64, change "handheld" to --3D pointing--.

Col. 17, line 47, change "features" to --feature--.

Col. 18, line 1, change "features" to --feature--; line 24, change "handheld" to --3D pointing--; and line 65, change "906" to --908--.

Col. 19, line 35, change "text" to --test--.

In the Claims:
Col. 20, claim 2, line 63, change "along" to --relative to--; and line 64, change "along" to --relative to--.

Col. 21, claim 3, line 5, change "along" to --relative to--; and line 7, change "along" to --relative to--.